United States Patent
Goemann-Thoss et al.

(10) Patent No.: US 10,551,397 B2
(45) Date of Patent: Feb. 4, 2020

(54) SYSTEM COMPRISING AT LEAST TWO LABORATORY INSTRUMENTS FOR INSTRUMENT-CONTROLLED HANDLING OF A PARTIAL PROBLEM IN A TREATMENT PROCESS CONTAINING TREATMENTS OF AT LEAST ONE LABORATORY SAMPLE, LABORATORY INSTRUMENT AND METHOD

(71) Applicant: Eppendorf AG, Hamburg (DE)

(72) Inventors: Wolfgang Goemann-Thoss, Hamburg (DE); Wolf Wente, Hamburg (DE); Andreas Thieme, Hamburg (DE); Jan-Gerd Frerichs, Norderstedt (DE); Christiane Markau, Hamburg (DE); Jan-Hendrik Hacker, Hamburg (DE)

( * ) Notice: Subject to any disclaimer, the term of this patent is extended or adjusted under 35 U.S.C. 154(b) by 0 days.

(21) Appl. No.: 14/508,716

(22) Filed: Oct. 7, 2014

(65) Prior Publication Data
US 2015/0104796 A1    Apr. 16, 2015

(30) Foreign Application Priority Data
Oct. 7, 2013   (EP) .................................... 13004813

(51) Int. Cl.
*G01N 35/00*   (2006.01)
(52) U.S. Cl.
CPC ... *G01N 35/00871* (2013.01); *G01N 35/0092* (2013.01); *G01N 2035/0091* (2013.01);
(Continued)

(58) Field of Classification Search
CPC ......... G01N 35/0087; G01N 35/00722; G01N 35/00584; G01N 35/0092; G01N 35/00;
(Continued)

(56) References Cited

U.S. PATENT DOCUMENTS

| 6,544,476 B1 | 4/2003 | Mimura et al. |
| 7,593,787 B2 | 9/2009 | Feingold et al. |

(Continued)

FOREIGN PATENT DOCUMENTS

| EP | 0952452 A1 | 10/1999 |
| EP | 0973115 A2 | 1/2000 |

(Continued)

OTHER PUBLICATIONS

International Search Report, dated Jan. 12, 2015, pp. 1-5, obtained on May 31, 2015.*

(Continued)

*Primary Examiner* — Christine T Mui
(74) *Attorney, Agent, or Firm* — Todd A. Lorenz

(57) ABSTRACT

The invention relates to a laboratory instrument for the instrument-controlled handling of a partial problem in a treatment process which contains treatments of at least one laboratory sample. The invention moreover relates to a system containing a plurality of such laboratory instruments, wherein the system serves for the instrument-controlled handling of a problem containing a plurality of these partial problems in the treatment process of at least one laboratory sample. And the invention relates to a method for the instrument-controlled handling of a partial problem in a treatment process which contains treatments of at least one laboratory sample.

24 Claims, 5 Drawing Sheets

(52) U.S. Cl.
CPC ............... *G01N 2035/0094* (2013.01); *G01N 2035/00881* (2013.01); *Y10T 436/11* (2015.01)

(58) Field of Classification Search
CPC ... G01N 2035/0094; G01N 2035/0091; G01N 2035/00881; Y10T 436/11; Y10T 436/00
USPC .......... 436/43, 63; 422/67, 63, 50; 435/6.12, 435/6.1, 287.2, 871.1, 283.1
See application file for complete search history.

(56) References Cited

U.S. PATENT DOCUMENTS

| | | |
|---|---|---|
| 2002/0032762 A1 | 3/2002 | Price et al. |
| 2002/0135678 A1 | 9/2002 | Bacus |
| 2003/0141116 A1 | 7/2003 | Nuesch et al. |
| 2004/0171171 A1 | 9/2004 | Appoldt et al. |
| 2005/0014285 A1 | 1/2005 | Miller |
| 2005/0112542 A1 | 5/2005 | West |
| 2005/0131734 A1 | 6/2005 | Sugiyama |
| 2005/0159982 A1 | 7/2005 | Showalter et al. |
| 2005/0192908 A1 | 9/2005 | Jorimann et al. |
| 2006/0173575 A1 | 8/2006 | Lefebvre et al. |
| 2006/0242276 A1 | 10/2006 | Price et al. |
| 2007/0143465 A1 | 6/2007 | Gonzalez et al. |
| 2007/0233303 A1 | 10/2007 | Naito et al. |
| 2007/0255756 A1 | 11/2007 | Satomura et al. |
| 2008/0059472 A1 | 3/2008 | Yamamoto et al. |
| 2008/0256227 A1 | 10/2008 | Malin |
| 2010/0106427 A1 | 4/2010 | Fukuma et al. |
| 2010/0271479 A1 | 10/2010 | Heydlauf |
| 2011/0246215 A1 | 10/2011 | Postma et al. |
| 2013/0045473 A1 | 2/2013 | Duerr et al. |
| 2013/0159135 A1 | 6/2013 | Jones et al. |

FOREIGN PATENT DOCUMENTS

| | | | |
|---|---|---|---|
| EP | 1248170 A1 | 10/2002 | |
| EP | 1840576 A2 | 10/2007 | |
| EP | 1981245 A1 | 10/2008 | |
| EP | 2182364 A2 | 5/2010 | |
| EP | 2182365 A2 | 5/2010 | |
| EP | 2299277 A1 | 3/2011 | |
| EP | 2 450 711 A1 * | 5/2012 | .......... G05B 19/418 |
| EP | 2450711 A1 | 5/2012 | |
| WO | WO 1994011838 A1 | 5/1994 | |
| WO | WO 2008012104 A2 | 1/2008 | |
| WO | WO 2009085534 A1 | 7/2009 | |
| WO | WO 2012/045415 A1 * | 4/2012 | ............. G01N 35/00 |

OTHER PUBLICATIONS

Written Opinion of PCT/EP2014/002716, dated Jan. 12, 2015, pp. 1-6, obtained on May 31, 2015.*

U.S. Appl. No. 14/508,703 (U.S. Publication No. US 2015-0125961 A1), entitled, "Laboratory instrument with access control device and method for instrument-controlled treatment of laboratory samples," filed Oct. 7, 2014, of Goemann-Thoss, et al.

U.S. Appl. No. 14/508,722 (U.S. Publication No. US 2015-0105877 A1), entitled, "Configuration control device for a laboratory instrument, laboratory instrument with the configuration control device for instrument-controlled treatment of at least one laboratory sample and a method for configuring the laboratory instrument by means of the configuration control device," filed Oct. 7, 2014, of Goemann-Thoss, et al.

U.S. Appl. No. 14/508,724 (U.S. Publication No. US 2015-0127270 A1), entitled, "Laboratory instrument, system and method for instrument-controlled treatment of at least one laboratory sample using at least one consumable," filed Oct. 7, 2014, of Goemann-Thoss, et al.

* cited by examiner

SYSTEM COMPRISING AT LEAST TWO LABORATORY INSTRUMENTS FOR INSTRUMENT-CONTROLLED HANDLING OF A PARTIAL PROBLEM IN A TREATMENT PROCESS CONTAINING TREATMENTS OF AT LEAST ONE LABORATORY SAMPLE, LABORATORY INSTRUMENT AND METHOD

The invention relates to a laboratory instrument for the instrument-controlled handling of a partial problem in a treatment process which contains treatments of at least one laboratory sample. The invention moreover relates to a system containing a plurality of such laboratory instrument, wherein the system serves for the instrument-controlled handling of one of these problems containing a plurality of partial problems in the treatment process of at least one laboratory sample. And the invention relates to a method for the instrument-controlled handling of a partial problem in a treatment process which contains treatments of at least one laboratory sample.

Laboratory instruments are used in chemical, biological, biochemical, medical or forensic laboratories to handle laboratory samples, in particular liquid laboratory samples, with great efficiency. Laboratory instruments at least partly automate treatment steps which would otherwise have to be performed manually and thus increase the speed, precision and reliability of these treatments. A treatment of laboratory samples, which are usually in liquid form, may be directed to modifying or examining or analysing these laboratory samples, in particular the composition thereof, in a physical, chemical, biochemical or other manner.

Laboratory instruments comprise at least one treatment apparatus for instrument-controlled treatment of the at least one laboratory sample. They often have a program control, by means of which a user of the laboratory instrument can set the treatment to be performed by setting the desired program parameters. The program parameters are set by means of an operating unit of the laboratory instrument, which enables the input and output of information, in particular of values of the program parameters.

Within the scope of working on laboratory samples in laboratories, a multiplicity of laboratory instruments are often required to successfully complete a complicated problem. Obtaining DNA from forensic samples may serve as an example. Chelex extraction is a DNA isolation process that is conventional in forensics. Chelex consists of artificial resin particles, which serve as a carrier for a chelator bound to the surface. Chelex binds divalent ions such as $Mg^{2+}$ or $Ca^{2+}$ and inactivates in the solution enzymes, which are determined thereby and are unwanted in the scope of obtaining DNA, such as e.g. DNases. As a side effect, the cytoskeleton of a cell or specific extracellular structural proteins are inactivated, which destabilizes the cell in an undesired manner. Addition of proteinase K leads to the degradation of the unwanted enzymes and structural proteins and ultimately leads to the degradation of the cell in a desired manner, releasing the DNA to be obtained in the process. The proteinase is deactivated by boiling since these would, in particular, hinder the PCR (polymerase chain reaction), by means of which the traces of DNA are ultimately multiplied. In order to obtain DNA from a blood sample, e.g. the following steps are conventional in this method. If a multiplicity of samples needs to be processed, laboratory instruments are used, by means of which it is possible to process a multiplicity of samples in parallel:

1. Transfer blood into 1.5 ml tubules; addition of sterile Aqua bidest.; incubation of the samples at room temperature. For these steps, use is made e.g. of a laboratory machine (pipetting machine) for the treatment of liquid samples.
2. Centrifuge samples. For this step, use is made of a laboratory centrifuge.
3. Removal of the aqueous supernatant such that the sample remains in the sample tubule with little liquid. Addition of chelex and proteinase K. To this end, use is made of a laboratory machine (pipetting machine) for treatment of liquid samples, which can, in particular, also mix samples since it has a mixing instrument, in particular also a temperature-controllable mixing instrument, integrated therein.
4. Samples are incubated in a water bath at 56° C. under light shaking. To this end, use is made of e.g. an incubator with an integrated laboratory shaker or else a temperature-controllable mixing instrument.
5. Samples are mixed. To this end, use is made of the laboratory machine (pipetting machine) for treatment of liquid samples, which can, in particular, also mix samples since it has a mixing instrument, in particular also a temperature-controllable mixing instrument, integrated therein.
6. Samples are incubated at 100° C., and then at 4° C. To this end, use is made of e.g. an incubator with an integrated laboratory shaker or else a temperature-controllable mixing instrument.
7. Samples are mixed again. To this end, use is made of the laboratory machine for treatment of liquid samples, which can, in particular, also mix samples since it has a mixing instrument, in particular also a temperature-controllable mixing instrument, integrated therein.
8. Samples are centrifuged. For this step, use is made of a laboratory centrifuge.
9. Samples are amplified by means of PCR. To this end, use is made of e.g. a laboratory machine for treatment of liquid samples, in particular comprising an integrated thermocycler by means of which the PCR proceeds in an automated manner.
10. If need be, some of the samples are frozen. To this end, use is made of a laboratory freezer.

The problem underlying this treatment process, namely obtaining a desired amount of DNA from a blood sample, can be subdivided into the aforementioned partial problems numbered 1 to 10. Each partial problem contains a treatment of the laboratory samples in a predetermined manner and in each case requires a specific laboratory instrument.

Usually, the laboratory technician determines the boundary conditions for the treatment of the samples at the respective laboratory instrument when carrying out these steps. These boundary conditions include the question whether a laboratory instrument required for handling the partial problem at a specific time is available. Furthermore, a certain amount of consumable material must be kept available so that a treatment can run in each case without delay. Moreover, the laboratory technician must react flexibly if unexpected events occur during a partial problem, e.g. a loss of a sample or a supply bottleneck in the case of laboratory resources, e.g. laboratory instruments or consumable material. To this end, he requires the corresponding information in order, for example, to be able to undertake suitable adaptations in a subsequent treatment at the next laboratory instrument. The aforementioned steps are complicated and, in practice, lead to delays in laboratory work, as a result of which the efficiency of the workflow is reduced.

The prior art knows laboratory systems, which are fully automated and have a central control using a central computer. The procedure related to a partial problem is executed, respectively, by a working device, which is formed as a part of the laboratory system. For the purpose of achieving the respective function, the known laboratory systems are configured to send data to the central computer via an interface device or receive control data from the same, respectively. The parts of said laboratory systems form a network having star-topology, wherein the working devices have a data connection with the central computer, but wherein the working devices are not connected with each other. The working devices are no laboratory devices and, in this sense, are not stand-alone devices capable to work independently. Said fully automated laboratory systems are expensive and do not offer the most efficient solution for solving problems or partial problems typically encountered in laboratories.

EP 2 450 711 A1 describes instruments, which form the working devices of such a fully automated laboratory system, which each are connected with an instrument manager or a process sample manager for data exchange. EP 2 182 365 A2 describes a fully automated laboratory system for the size measurements on blood cells, wherein detectors serve as working devices, whose measurement data are received by a central controller. WO 2008/012104 A2 describes a sample processing device for the treatment of biological samples, which after being started continuously and independently and without a user intervention processes a process chain. The working devices are formed by modules, which a controlled by a central control module via a CAN bus for processing a problem-related procedure and which are therefore capable to function in combination. EP 1 248 170 A1 describes work cell systems, which are configured for controlling working devices, referred to as resources, which are connected, respectively, with a central automation management system for achieving an automated processing of procedures for solving a problem in medical laboratories.

It is the object of the present invention to improve the workflow during instrument-controlled handling of a problem or partial problem in a treatment process containing treatments of at least one laboratory sample.

The invention achieves this object by means of, in particular, the system in accordance with claim 1, the laboratory instrument in accordance with claim 7 and the methods according to claims 8 and 9. Preferred embodiments of the invention are, in particular, the subject matter of the dependent claims.

The laboratory instrument according to the invention serves for the instrument controlled treatment of a partial problem in a treatment process for handling at least one laboratory sample, which treatment process relates to the handling of a problem comprising partial problems when handling the at least one laboratory sample using the laboratory instrument and at least one further laboratory instrument. In particular, the laboratory instrument according to the invention comprises:
- a treatment apparatus for the instrument-controlled handling of the partial problem,
- a control apparatus for controlling the laboratory instrument,
- at least one interface apparatus for establishing at least one data connection to at least one further laboratory instrument;

wherein the control apparatus is configured:
- to receive first treatment data, which can be used for handling the partial problem, via the at least one interface apparatus and
- to perform the control of the handling of the partial problem using these first treatment data,
- to provide, in particular generate, second treatment data as a function of the handling of the partial problem, which second treatment data can be used by the further laboratory instrument for handling a further partial problem of the treatment process, and
- to output at least these further treatment data for use by the further laboratory instrument via the at least one interface apparatus.

In the following, the "further treatment data" are also referred to as "second treatment data".

The laboratory instrument according to the invention offers the advantage of providing second treatment data which arise when performing the treatment on the laboratory instrument. In particular, these second data represent information which is required for performing a further treatment on a further laboratory instrument within the scope of performing the treatment process. As a result, the further treatment can be performed in a more efficient manner, in particular if use is made of a system with a plurality of such laboratory instruments for performing a complex problem. The configuration of the laboratory instrument according to the invention renders it possible to use it in a system according to the invention, which is designed as follows:

The system according to the invention serves for instrument-controlled handling of a problem by a treatment process for handling at least one laboratory sample, wherein the problem contains the handling of at least a first and/or a second partial problem, wherein the system comprises:
- at least a first laboratory instrument according to the invention for handling the first partial problem of the problem, and
- at least a second laboratory instrument according to the invention for handling the second partial problem of the problem, wherein the first laboratory instrument is configured
- to perform the control of the handling of the partial problem using first treatment data, wherein the system is configured:
- to provide, in particular generate, second treatment data as a function of the handling of the first partial problem, which second treatment data can be used by the second laboratory instrument for handling the second partial problem of the treatment process, and
- to output at least these second treatment data for use by the at least one second laboratory instrument via the at least one interface apparatus.

wherein the second laboratory instrument is configured
- to receive second treatment data, which can be used for handling the second partial problem, via the at least one interface apparatus and
- to perform the control of the program-controlled handling of the second partial problem using second treatment data, The term "treatment" means, in particular, that a laboratory sample, which is usually in liquid form, is moved, transported and/or examined and/or modified, in particular modified physically, chemically, biochemically or in another way in terms of the composition thereof.

Treatment data, in particular the first and/or the second treatment data, preferably in each case contain process data. The term "process" denotes the treatment process. In particular, process data contain information which is essential for performing the treatment process or for performing at least one treatment of the treatment process. Such process data can change during the treatment process and/or during an individual treatment of the treatment process. By way of example, it is possible to establish a substance concentration during a measurement of samples on a first laboratory instrument, e.g. if this first laboratory instrument is a biospectrometer. As a result of the substance concentration, a specific dilution series may become necessary, which requires a specific dilution series in the further treatment step on a further laboratory instrument, e.g. a pipetting machine. The information about the concentration is only generated on the first laboratory instrument, and so the further procedure can, as a matter of principle, only be planned from this time. Then, the process data can either contain information about the substance concentration and/or the desired target concentration(s) or information for defining a dilution series. In any case, the further laboratory instrument, in this example here the further laboratory machine (pipetting machine), can start with the desired dilution series without delay. Particularly in this context, it is particularly advantageous if process data are provided as second treatment data with such essential information for the further treatment from the laboratory instrument that they can be used on the subsequent, i.e. "further" or "second", laboratory instrument without there being a delay in the provision of the data.

The first and/or the second treatment data can respectively contain time data which contain information about the planned start and/or the end of a treatment. The time data can contain information about absolute times or about relative times and/or periods of time.

The first and/or the second treatment data can respectively contain sample data. The sample data can contain information about the number of laboratory samples to be treated, the type of the laboratory samples to be treated, the amount of individual laboratory samples or the total amount of the laboratory samples or a category of the laboratory samples. The sample data can contain information about laboratory containers with samples, in particular about the sample tubules or microtitre plates, in particular the fill state or occupancy state or the size thereof. The sample data can contain information about treatment prescriptions for the laboratory samples or individual laboratory samples, e.g. information about processing times, incubation times or sample temperatures to be maintained, or data for individualization of the samples, e.g. with the goal of a unique patient assignment to the samples.

The first and/or the second treatment data can respectively contain commodity data. The commodity data can contain information about commodities used or required in a specific treatment, e.g. laboratory containers, in particular sample tubules or microtitre plates, or e.g. transport containers, in particular pipette tips or dispenser tips. The commodity data can contain information about solvents, nutrient solutions, a cleaning fluid, buffers or other non-solid consumables, which are expected during an individual treatment.

The first and/or the second treatment data can respectively contain user data. The user data can contain information about the user who has started a treatment process, in particular identification data or an identification code, by means of which the user is uniquely identifiable. The user data can contain information about the role or group membership of a user. The user data can contain information about the authorizations and/or access permissions of a user.

The first and/or the second treatment data can respectively contain program data, in particular program parameters or information relating thereto.

The instrument-controlled treatment in the case of a laboratory instrument preferably takes place using at least one program parameter. Preferably, the treatment performed by the treatment apparatus of a laboratory instrument is a program-controlled treatment. Preferably, the program-controlled treatment takes place using at least one program parameter. The latter can be a user parameter. The at least one program parameter can be a constituent of the first and/or the second treatment data or can be established uniquely by the control apparatus of a laboratory instrument from the first and/or the second treatment data.

Preferably, the system comprises at least one external data processing instrument, which is also referred to as data processing apparatus and which can, in particular, be a computer or comprise a computer. The external data processing instrument can, in particular, be a server. A server is, in particular, a computer, the hardware of which is preferably tuned to server applications.

The external data processing instrument preferably comprises in each case: at least one storage apparatus for volatile and/or permanent storage of data; at least one control apparatus; at least one communication apparatus; at least one interface apparatus.

Within the scope of the present invention, a control apparatus generally comprises, in particular, a data processing apparatus, in particular a computer unit (CPU) for processing data. The computer unit is preferably also configured for controlling the external data processing instrument and/or the treatment process and/or the individual treatments.

A communication apparatus is preferably configured for the transmission and/or reception of data, in particular the data interchange via a remote data connection provided by the communication apparatus to an instrument at a distance, which is also referred to as a "remote instrument". The remote data connection can be established by a restricted network of computers (in particular an intranet) or over a worldwide network of computers (in particular the Internet). The remote data connection can also be established over a wireless connection. The remote data connection can, in particular, be established over a mobile communications connection.

Preferably, in a first preferred configuration of the system according to the invention, the at least one external data processing apparatus comprises at least one storage apparatus, in which first and/or second treatment data, which are used for performing the treatment process, can be stored.

Preferably, in a second preferred configuration of the system according to the invention which can, in particular, comprise the first configuration, the at least one external data processing apparatus is configured to process first and/or second treatment data from at least one laboratory instrument of the system during the treatment process, in particular to receive treatment data from the first laboratory instrument and transmit treatment data to the second laboratory instrument.

Preferably, in a third preferred configuration of the system according to the invention which can, in particular, comprise the first or second configuration, the system comprises at least one user interface apparatus, by means of which treatment data, in particular first and/or second treatment data, can be determined by a user. The user interface apparatus is preferably embodied to output the treatment data to at least one laboratory instrument, in particular to at least one external data processing instrument.

Preferably, in a fourth preferred configuration of the system according to the invention which can, in particular, comprise the first, second or third configuration, at least one first laboratory instrument is configured to generate at least one first data record during the handling of a partial problem, which data record in particular contains information about the performance of the treatment in accordance with the first partial problem, in particular log data or consumable material-related data, and to output this data record via the at least one interface apparatus, in particular to the at least one second laboratory instrument or an external data processing instrument. Furthermore, the system is preferably configured to collect and store the at least one first data record in a database.

Preferably, in a fifth preferred configuration of the system according to the invention which can, in particular, comprise the first, second, third or fourth configuration, the system comprises at least one data-processing apparatus belonging to the system, in particular a computer, which is configured to receive and/or transmit and/or store treatment data. Preferably, this computer is embodied to collect log data about a process. Preferably, the computer is a dedicated server which, in particular, is not a laboratory instrument with a treatment apparatus, as defined within the scope of this description. However, it is also possible that a laboratory instrument is configured in such a way that it assumes the functions of the server, wherein such a server is not a dedicated server.

The log data preferably contain at least first and/or second treatment data, preferably all first and/or second treatment data which are provided and/or generated by at least one, a plurality of or all laboratory instruments of the system during the course of the treatment process. In this manner, an electronic lab book can be generated, by means of which the individual treatments of the treatment process are compiled and stored as a file, in particular depending on user data, in particular on the identity of the user performing the treatments or the treatment process. This lab book aids the quality control in a laboratory. There are also cases in which the generation of a lab book is essential in order to substantiate the performed treatments or the performed treatment process. The efficiency of a laboratory is significantly increased by the electronic lab book.

Preferably, the log data contain all treatment data required for being able to unambiguously reproduce the treatment process with the system. A certification file for the treatment process can be generated on the basis of such treatment data. The treatment process can be repeated and/or verified with the aid of the certification file.

Preferably, the system comprises a computer, in particular a server, which comprises a booking database. The latter can comprise a calendar in which entries relating to the temporal use of one or more laboratory instruments can be entered with a predetermined temporal accuracy, e.g. occupation down to a minute. Preferably, the system is configured to manage the use of one, a plurality of or all of the laboratory instruments of the system by means of the booking database. Preferably, the computer is configured to set a temporal booking of the laboratory instruments required for the treatment process, taking into account the information contained in the booking database regarding the temporal reservation of one or more laboratory instruments required for a treatment process, and to enter this booking into the booking database in particular. Accordingly, the entries in the booking database can be, firstly, brought about by the computer or, secondly, entered by one or more users. As a result, the efficiency in a laboratory is improved further.

Preferably, the computer is configured to receive user data which a user transmits to the computer, in particular with the aid of an external data processing instrument, in particular via a communication apparatus of the computer or via an interface apparatus of the computer. Preferably, the computer is configured to define the treatment process from these user data. In the process, the laboratory instruments required for performing the treatment process desired by the user and how the treatments are performed, in particular dependent on the role, qualification or group membership of the user and in particular taking into account the bookings of the laboratory instruments required for this treatment process, are preferably set. However, the treatment process can also already be planned and be available in the form of a generation file, which defines the treatment process in a sufficient, in particular unique manner. The computer plans and/or manages and/or controls preferably the whole treatment process or parts thereof.

It is preferable for the laboratory instrument to transmit the provided and/or generated treatment data, in particular the "further" or "second" treatment data, directly to the computer, in particular the server, i.e. transmit the data via a direct wireless or wired data connection to the computer, in particular to the server. It is also preferable for the laboratory instrument to transmit the provided and/or generated treatment data, in particular the "further" or "second" treatment data, indirectly, i.e. non-directly, to the computer, in particular the server, i.e. transmit the data via an indirect wireless or wired data connection to the computer, in particular to the server. Here, at least one further data processing instrument, which receives and forwards the treatment data, can be interposed. This data processing instrument can be a laboratory instrument or the control apparatus thereof, or a different computer.

It is preferred that the laboratory instrument transfers the treatment data, which have been provided or generated, in particular the "further treatment data" or "second treatment data", via the interface apparatus directly to a further laboratory instrument, wherein the transfer may use a direct wireless or direct wired data connection. It is also preferred that the laboratory instrument transfers the treatment data, which have been provided or generated, in particular the "further treatment data" or "second treatment data", indirectly, i.e. using one or more interconnected devices, to a further laboratory instrument, wherein the transfer may use an indirect wireless or indirect wired data connection. Both configurations allow for a more flexible design of the system according to the invention, wherein the optional central control apparatus of the system, in particular the control apparatus of an optional external data processing apparatus can be unburdened or may even be omitted. In particular in this case, the control of the treatment process may be conducted by the control apparatus of a laboratory instrument, or may be passed from the laboratory instrument to the further laboratory instrument. It is also possible and preferable for the system not to comprise a computer, in particular not to comprise a server.

Preferably, the laboratory instruments of a system are networked together, i.e. each laboratory instrument is configured to establish a data connection to at least one other laboratory instrument of the system. It can be a wireless or wired connection. The network can comprise a serial arrangement of the laboratory instruments, which are logically disposed in succession and which are preferably used in this sequence, or else in a different sequence, during a treatment process. The arrangement can be in the form of a chain, but it can also be in the form of a ring or a star or it can be networked differently.

The preferred embodiment of the invention, where a laboratory instrument is configured to establish a data connection to at least one other laboratory instrument of the system, achieves the advantage that a more flexible design of the system according to the invention becomes possible. A laboratory instrument can transfer the second treatment data to the further laboratory instrument without the need to let the second treatment data be evaluated by a control apparatus of an external data processing apparatus or another interconnected device. The further laboratory device receives the second treatment data and can use, e.g. evaluate, the same directly for handling the second partial problem. The transfer of the second treatment data, or respectively the multiple transfers of treatment data from one laboratory instrument to a further laboratory instrument in case of multiple laboratory instruments in a system, allows for an efficient handling of the problem. The treatment data, in particular the first and/or second and/or further treatment data may contain, in particular, process data, or values of process parameters, which are required for handling the overall problem by handling the partial problems. Preferably, a laboratory instrument has a user interface apparatus comprising a display, by means of which one or more process parameters or other data may be displayed or may be graphically represented for informing the user about the progress of processing the problem and/or one or more partial problems and/or the process data or value of one or more process parameter, respectively.

Preferably, the laboratory instrument is configured to provide, in particular generate, second treatment data as a function of the handling of the first partial problem, which second treatment data can be used by the second laboratory instrument for handling the second partial problem of the treatment process, and to output at least these second treatment data for use by the at least one second laboratory instrument.

Preferably, a first laboratory instrument of the system is embodied to receive user data which a user transmits to the laboratory instrument, in particular with the aid of an external data processing instrument, in particular via an optional communication apparatus of the laboratory instrument or via an interface apparatus of the laboratory instrument. Preferably, the laboratory instrument or the system is configured to define the treatment process from these user data. In the process, the laboratory instruments required for performing the treatment process desired by the user and/or how the treatments are performed, in particular dependent on the role, qualification or group membership of the user and/or in particular taking into account the bookings of the laboratory instruments required for this treatment process, are preferably set. However, the treatment process can also already be planned and be available in the form of a generation file, which defines the treatment process in a sufficient, in particular unique manner. The laboratory instruments of a system, in particular of a system which does not comprise a server or a dedicated server, are preferably configured to plan and/or manage and/or control the treatment process. Each laboratory instrument is preferably embodied to receive, bundle when necessary and/or forward, in particular to a further laboratory instrument and/or an external data processing instrument, the treatment data required for performing the further treatment step, in particular parameters and/or process data. In this system, it is also possible to generate an electronic lab book, a log file or a certification file and, in particular, provide this at the end of a treatment process for further use.

The invention moreover relates to a method for instrument-controlled handling of a partial problem in a treatment process for handling at least one laboratory sample, which treatment process relates to the handling of a problem comprising partial problems when handling the at least one laboratory sample using the laboratory instrument according to the invention, and carries out the following steps of the method by means of the control apparatus of the laboratory instrument:
  receiving first treatment data, which can be used for handling the partial problem, by means of the at least one interface apparatus of the laboratory instrument, and
  controlling the handling of the partial problem using these first treatment data,
  providing, in particular generating, further treatment data as a function of the handling of the partial problem, wherein the further treatment data can be used by a further laboratory instrument for handling a further partial problem of the treatment process, and
  outputting at least these further treatment data via the at least one interface apparatus for use by the further laboratory instrument.

The invention furthermore relates to the method for instrument-controlled handling of a problem by a treatment process for handling at least one laboratory sample, wherein the problem contains the handling of at least a first and a second partial problem using the system according to the invention, wherein the method comprises the following steps:
  controlling the handling of the first partial problem using first treatment data by means of the first laboratory instrument,
  providing, in particular generating, second treatment data, in particular as a function of the handling of the first partial problem, wherein the second treatment data can be used for handling the second partial problem of the treatment process by the second laboratory instrument,
  outputting at least these second treatment data for use by the at least one second laboratory instrument,
  receiving these second treatment data via the at least one interface apparatus at the second laboratory instrument, and
  controlling the handling of the second partial problem using these second treatment data by the second laboratory instrument.

Preferably, the laboratory instrument comprises an access control device in order to authenticate and/or authorize one or more users on the laboratory instrument. As a result, the system can, in particular, identify whether, within the scope of a treatment process to be performed, a laboratory instrument is used by a user who also initiated the treatment process.

In a laboratory instrument, the access control device preferably enables the access of one or more further users to the laboratory device to be controlled when a first user is already logged on and the session of said first user is still running on the laboratory instrument, i.e. when the access of the further user still is active. As a result of this embodiment, the laboratory instrument can be used more efficiently and the productivity of the laboratory can be improved.

The access control device is an apparatus configured for data processing. It serves for access control. The access control device comprises a control apparatus. The control apparatus is embodied for data processing. In particular, the control apparatus is an electronic control apparatus. It preferably has a data processing apparatus which, in particular, is electronic. The access control device preferably comprises at least one interface apparatus, by means of which the control apparatus can establish at least one first data connection to a user interface apparatus and preferably can establish at least one second data connection to an interface apparatus of the laboratory instrument or of an external data processing apparatus.

An interface apparatus serves for connecting two apparatuses which can each process, in particular transmit and/or receive, signals, in particular information, in particular data. An interface apparatus can contain at least one hardware interface and/or at least one software interface.

Hardware interfaces are, in particular, interfaces between electrically operating units in accordance with the usual understanding in electrical engineering and electronics. Presently, the phrase "hardware interface" in particular also denotes the connection components between at least two electrically operating units themselves, i.e., in particular, all constituents which enable this connection, e.g. integrated circuits, electronics and lines, by means of which electrical signals are transmitted between the at least two electrically operating units. In particular, these two electrically operating units can be a laboratory instrument and an external data processing apparatus or two laboratory instruments, or two electrically operating units, within a laboratory instrument. A hardware interface need not, but can, comprise a detachable connection apparatus for releasing and/or re-establishing this connection, in particular at least one connector.

Software interfaces, in particular software-side data interfaces, are, in particular, logical connection points in an information management system, in particular a software system: they enable and regulate the interchange of commands and data between various processes and components. Software interfaces may be data-oriented interfaces used for communication purposes only. In this case, the software interface merely contains information which is interchanged between involved system parts.

Within the scope of the present invention, a control apparatus generally comprises, in particular, a data processing apparatus, in particular a computer unit (CPU) for processing data and/or a microprocessor, or said control apparatus is a data processing apparatus. The computer unit of the control apparatus of a laboratory instrument is preferably also configured for controlling the treatment process and/or the individual treatments.

The control apparatus of the laboratory instrument and/or the optional access control and/or the optional user interface apparatus—in particular all of these—can be integrated in a physical instrument unit but can also in each case be independent physical instrument units. A physical instrument unit can, in particular, be a module which is or can be connected to the laboratory instrument. The control apparatus of the laboratory instrument and/or the optional access control device and/or the optional user interface apparatus or components of these components can also be implemented by software functions or can, in particular, be available as program code. By way of example, a laboratory instrument can comprise a computer which, in combination with software functions, in each case at least partly implements the control apparatus of the laboratory instrument and/or the optional access control device and/or the optional user interface apparatus. By way of example, if the access control device is integrated into the laboratory instrument, the access control device itself may be part of the control apparatus of the laboratory instrument or be implemented by means of the control apparatus, in particular by software functions, in particular at least partly as executable program code.

A module can, in particular, comprise the access control device and/or a user interface apparatus. A module is an instrument which is separate from other instruments and/or an instrument which can be separated from the other instrument, in particular the laboratory instrument. A laboratory instrument may comprise a connection apparatus, by means of which the module can be connected to the laboratory instrument, in particular by means of a connection which is detachable by the user. A module may be portable, i.e. transportable by a user. The module can also be securely connected to the laboratory instrument. The modular design offers advantages during the production of laboratory instruments. A portable module offers greater flexibility when using a laboratory instrument.

A communication apparatus is preferably configured for the transmission and/or reception of data, in particular the data interchange via a data connection provided by the communication apparatus, in particular a remote data connection to a remote instrument. In particular, the instrument arranged at a distance from a laboratory instrument is also referred to as "remote instrument" or external instrument. In particular, a data processing apparatus which is not a component of a laboratory instrument is also referred to as an external data processing apparatus. The data connection, in particular the remote data connection, can be established over a restricted network of computers (in particular an intranet) or over a worldwide network of computers (in particular the Internet). The data connection, in particular the remote data connection, can also be established over a wireless connection. The data connection, in particular the remote data connection, can, in particular, be established over a mobile communications connection.

A data connection connects, in particular, two data-processing units, in particular two data processing apparatuses, in such a way that data can be interchanged, either unidirectional or bidirectionally, between the units. The data connection can be realized with, or without, cables, in particular as a wireless connection. A remote data connection connects, in particular, two data processing units, in particular two data processing apparatuses, which are arranged at a distance from one another, which are therefore, in particular, not components of the same instrument, in particular of the same access control device, user Interface apparatus or of the same laboratory instrument if the aforementioned instruments are embodied as separate instruments. A data connection, in particular a remote data connection, from one instrument to another instrument is preferably realized by a direct connection between the two instruments or by means of an indirect connection between the two instruments such that a third instrument is switched between the two instruments in order to forward the data. In particular, a remote data connection can be realized via a network of computers, in the case of which the instruments connected via the remote data connection are connected via the network. The network can be a restricted network, e.g. an intranet, or a world-wide network, in particular the Internet.

A data processing apparatus preferably comprises a computer unit, in particular a CPU, furthermore preferably at least one data storage apparatus, in particular for temporary and/or permanent storage of data.

Every user can establish a first data connection with the access control device by means of the same user interface apparatus or a plurality of users can establish a first data connection with the access control device by means of different user interface apparatuses. A user interface apparatus can be a component of the access control device. An access control device can be a component of the user interface apparatus. A user interface apparatus can be a component of a laboratory instrument. A user interface apparatus preferably comprises in each case: a control apparatus for a user interface apparatus; a communication apparatus for establishing a data connection to a laboratory instrument by means of an interface apparatus of same; an input apparatus for acquiring user inputs of a user; an output apparatus, in particular an indication unit and/or a display, for outputting information to the user. Here, the control apparatus of the user interface apparatus is preferably configured to interchange data with the laboratory instrument via the data connection, which data were obtained from the user inputs and, in the laboratory instrument according to the invention, cause the user to be granted authorizations and/or access permissions on the laboratory instrument according to the invention, wherein a simultaneous log on and/or the simultaneous access of a first and at least a second user on the laboratory instrument according to the invention with respectively assigned access permissions to functions of the laboratory instrument can be controlled via the interface apparatus.

The access control device is preferably configured to control the access permissions by virtue of the control apparatus using a data connection to a database for access permissions. The database for access permissions is preferably stored in at least one, preferably in exactly one, storage apparatus for access permissions. The at least one storage apparatus for access permissions can be disposed in the access control device and/or it can be disposed in an external data processing apparatus. External means that the instrument, in this case the data processing apparatus, is not a constituent of the device in question, in this case the access control device. The database for access permissions can be stored centrally, but it can also be stored in a plurality of storage apparatuses which can each have some of the data in the database or else have a copy of the data in the database.

An external data processing apparatus can be a server, which is configured for establishing a data connection to more than one access control device and/or to more than one laboratory instrument. An external data processing apparatus can be a mobile data processing apparatus, which is configured for establishing a wireless data connection, in particular a data connection via a restricted computer network or a world-wide computer network. A computer network is a combination of various technical, primarily independent, electronic systems (in particular computers, but also sensors, actuators, agents and/or other radio components, etc.), which combination enables the communication between the individual systems.

The laboratory instrument, the control apparatus of the laboratory instrument or the control apparatus of the optional access control device can comprise a communication apparatus for establishing a data connection to an external data processing apparatus, in particular via an interface apparatus of the laboratory instrument. The access control device is preferably embodied to establish the access permissions using the data connection to the external data processing apparatus, in particular via an interface apparatus of the access control device. The external data processing apparatus preferably comprises at least part, or all of, the database for access permissions.

The control apparatus of the access control device is configured to control authorizations and/or access permissions for the access of users via the user interface apparatuses and the first and second data connections to functions of the laboratory instrument. As a result of this, a user-dependent use of the laboratory instrument is possible, which is controlled depending on the respectively allocated access permissions. In particular, simultaneous use of the laboratory instrument by at least a first and at least a second user is made possible.

The access control device performs the access control. The phrase "access control" denotes, in particular, methods for managing the requests for resources and/or data, which are managed by an information management system and which are handled for managing the decisions as to how the request is handled, in particular whether or not access is granted and/or in what manner the access is or is not granted. In particular, the information management system can be an operating system which is executed on the access control device. If the user of an information management system wishes to perform a specific operation on a specific resource and/or with specific data, the access control device makes a decision as to whether this request should in actual fact be granted or whether it should be denied. An access control decision (yes/no) relates to, in particular, an access control triple consisting of "subject", "object" and "operation".

In particular, an active entity of a system, wishing to perform a specific operation on a specific object, is referred to as a subject. In this context, an entity denotes a uniquely determinable unit, relating to which information is to be stored and/or processed. The unit may be material or immaterial, concrete or abstract. Subjects are, in particular, human users of an information management system or computer programs which are used by human users for completing tasks. A subject may also be a group of users, e.g. laboratory worker, servicing technician, administrator. Accordingly, the group combines a plurality of individual subjects.

A user may represent an individual, or a group of a plurality of individuals, or a class of individuals, which were selected in accordance with a class rule or role rule.

The access control device can preferably distinguish between the at least one first user and the at least one second user. A user is preferably uniquely identified by the access control device. To this end, the access control device preferably processes identification data. The access control device is preferably embodied to authenticate the requesting user, i.e. to perform a verification method, by means of which the authenticity of the requesting user is checked and the user is authenticated if the verification is positive. By way of example, authentication data contain a login text and a password text or a data set for facial recognition or for an iris scan or for a fingerprint scan, etc. Furthermore, authentication can be performed by means of an RFID chip or NFC chip, or via gesture identification. In particular, an authentication may be performed in situ by means of direct access to the laboratory instrument or the access control device thereof, or by means of remote access.

The access control device preferably comprises an information management system, by means of which the access control is realized. The information management system is preferably an operating system of a laboratory instrument and/or of the access control device thereof, by means of which the access control device and/or the laboratory instrument are operated.

The access control device is preferably embodied to log the requesting user, in particular a plurality of requesting users, in particular the at least one first user and the at least one second user, onto the access control device, in particular onto the information management system of the access control device. The log-on process is also referred to as logging in. The successfully logged-on user preferably receives predetermined authorizations and/or access permissions. The user himself can cancel being logged-on or this can be cancelled by other conditions, for example by the instrument-controlled logging-off of the user, in particular if a maximum logged-on time, during which the user was logged-on, without interruption, via the access control device is exceeded, or after a predetermined time of inactivity, or depending on the time of the end of the treatment performed by the user or due to individual process programming. Cancelling of logging on preferably means that the authorization granted during the log-on is revoked.

Logging into the information management system is preferably brought about by virtue of the user being authenticated. After authentication, the user obtains, for logging-in purposes, a personalized access to the information management system, with authorizations and/or access permissions, which are established by means of the database for access permissions. A session starts with the login and it is terminated by logging out, which is also referred to as logging off.

The access control device is preferably embodied to release the use of, i.e. authorize the authenticated user to use, the authorizations, operations and objects on the laboratory instrument or the functions and services of the laboratory instrument, which comprises the access control device, as a function of the predetermined access permissions. The access control device is preferably software controlled, in particular program controlled. LDAP (Lightweight Directory Access Protocol) is preferably used as application protocol when implementing the software functions.

The access control can take place in accordance with one or more specific data models. One such specific data model is, in particular, the access control model (ACM). In particular, the access control may comprise a so-called reference monitor. In particular, this component should be understood to be the functional core of the access control device. The reference monitor fulfils the function of deciding whether the access to an object, as desired by a subject, is granted. The access control device may preferably not release any access to a resource of the laboratory instrument without the reference monitor being used. The reference monitor preferably also satisfies the function of recording access attempts that took place.

The access control is preferably configured in accordance with one, or else in accordance with more, of the known basic forms DAC ("Discretionary Access Control"), MAC ("Mandatory Access Control") or RBAC ("Role-Based Access Control"), with RBAC being particularly preferred.

Preferably, the access control provides the use of at least one role, preferably of a plurality of roles, wherein, in particular, permissions are in each case combined within the role. The at least one role is preferably stored in the database for access permissions. In particular, a role is suitably adapted to a responsibility or a problem description within the scope of using a laboratory instrument, in particular within the business using the laboratory instrument and/or in the business which fulfils a servicing contract relating to the laboratory instrument by virtue of e.g. performing diagnostic functions on the laboratory instrument, and/or in the manufacturer of the laboratory instrument, which e.g. transmits firmware updates, calibrations or information about the laboratory instrument and/or the accessories thereof directly to the laboratory instrument via the access control device. In particular, such roles can combine permissions. Instead of storing a set of individual rights for each user, the latter can be assigned at least one role. The role assignment is particularly reliable in terms of the implementation and requires relatively little outlay, in particular management outlay when establishing and storing permissions.

The access control preferably provides for at least two, preferably a plurality of, roles. Possible roles are, in particular, administrator ("Admin"), maintenance, normal laboratory user ("LabUser"), inexperienced laboratory user ("Inexperienced"), manager. Such roles enable a secure and efficient access control. The use of a laboratory instrument provided with the access control device is safe and efficient. This prevents, in a simple manner, a user, for example due to lack of qualification, from performing certain operations on the laboratory instrument which could possibly lead to damage or inefficient use of the laboratory instrument or to increased costs during operation, e.g. due to excessive use of consumables used for a treatment.

The access control preferably provides at least one role, or more than one role, which can be assigned simultaneously to a user. Therefore, an individual can, for example, obtain access as administrator or as normal laboratory user, depending on a further condition. The user can preferably decide himself the role in which he obtains access to the laboratory instrument. However, it is also possible that the user does not decide this himself, but that this is decided by the access control device. This condition may be the data record used for authentication purposes, in particular the used password, or it may depend on a parameter of the laboratory instrument, in particular on an operating parameter of the laboratory instrument, e.g. an operating parameter which characterizes an error state of the laboratory instrument.

Preferably, the control apparatus of the access control device and/or the control apparatus of the laboratory instrument comprises a storage apparatus in which user qualification data are stored, which are assigned each user of the laboratory instrument qualification in the form of at least one qualification value or certificate. Preferably, the access control device, in particular the control apparatus of the access control device, is configured in such a way that the authorizations and/or access permissions are granted to a user, in particular, the latter is assigned a role, as a function of his qualifications. As a result of this, users may use the laboratory instrument in accordance with their qualification and, in particular, inexperienced users are not overwhelmed. As a result, the productivity and operational safety during use of the laboratory instrument are increased.

Preferably, the control apparatus of the access control device and/or the control apparatus of the laboratory instrument are embodied to carry out a qualification method for at least one user, in which the at least one user runs through a qualification exam, which is carried out and evaluated by the control apparatus, and wherein the qualification method in particular provides for the data entered by the at least one user as a response to specific questions to be evaluated and in particular provides for the at least one user to be assigned a qualification, in particular in accordance with a comparison table or a computational prescription, as a function of the result of this evaluation. Such a qualification method carried out on the access control device or on the laboratory instrument is particularly practically relevant and therefore efficient.

Preferably, the control apparatus of the access control device and/or the control apparatus of the laboratory instrument are embodied, by means of the access control device, to grant and/or withdraw certain access permissions to functions of the laboratory machine to or from the user, depending on his qualification.

Preferably, the control apparatus of the access control device and/or the control apparatus of the laboratory instrument are embodied to display to the user, depending on his qualification, at least one graphical user interface, which corresponds to the qualification, on the display of the user interface apparatus and/or, in particular, to make available or not make available certain assistance programs or auxiliary information.

Preferably, the control apparatus of the access control device and/or the control apparatus of the laboratory instrument comprises a timer, in particular a clock, and, in particular, a booking apparatus, which comprises a storage apparatus which stores booking data, which, in particular, contain at least one booking data record or a plurality of booking data records, which describe at least one booking schedule, in particular individually for each treatment apparatus.

A booking data record contains, in particular, at least one of the items of information, in particular, which user, in particular at what time, carries out, has carried out or will carry out, in particular, which treatment of samples, in particular by means of which the laboratory instrument. The booking data preferably contain information about the bookings accepted by the booking apparatus, which bookings were in fact confirmed after comparison with the free capacities present in the booking schedule and were recorded in the booking schedule. However, the booking data may also contain booking requests, which the booking apparatus can recheck, in particular even at a later time after the request was placed, and possibly accept at a later date, for example if an earlier entry in the reservation schedule was subsequently cancelled. The reservation data record preferably also contains information about what type of treatment is in each case planned on the laboratory instrument and/or information about the process program used, and preferably contains, in particular, at least one program parameter or control parameter.

Preferably, the access control device is configured to transmit to a user upon request at least one item of information about the booking schedule, in particular to transmit the whole or part of the booking schedule or to transmit at least one change in the booking schedule. Preferably, the access control device is configured to transmit a notification automatically to a user, depending on at least one condition. This condition could be the change in the reservation schedule of a laboratory instrument, in particular in relation to the availability of a date for carrying out a treatment, in particular the release or cancelling of a date.

The "type of treatment" is, in particular, predetermined by the program parameters characterizing treatment. Such program parameters are, in particular, used by the control apparatus to generate a process program. In particular, a process program is a control code for controlling the treatment by means of control parameters. In particular, the control parameters are generated by the control apparatus, in particular by a control program running on the control apparatus, e.g. an operating system, while using the program parameters. The treatment of a sample is carried out, in particular, by virtue of a process program being executed by the control apparatus.

A "type of treatment" means a process, namely a type of application (e.g. "MagSep Blood gDNA", "Compose Mastermix" etc.). In a preferred configuration of the laboratory instrument as laboratory machine, the user initially selects a desired application, i.e. a "type of treatment", by virtue of selecting an application, in particular on the touchscreen of an instrument. This application, which is also referred to as "process", is, in particular, assigned to a program module which, in particular, may be a constituent of the control program. In particular, at least one program parameter is queried by the user by means of the program module. A program module generates, in particular, a process program on the basis of the at least one program parameter selected by the user.

Preferably, the control apparatus of the access control device and/or the control apparatus of the laboratory instrument is embodied to store booking data in the storage apparatus of the booking apparatus.

Preferably, the control apparatus of the access control device and/or the control apparatus of the laboratory instrument is configured to record the booking data record entered by the user into the laboratory instrument, in particular by means of the user interface apparatus or a portable or mobile user interface apparatus.

Preferably, the control apparatus of the access control device and/or the control apparatus of the laboratory instrument is embodied to compare the booking data record entered by the user with booking data already stored in the storage apparatus of the user interface apparatus.

Preferably, the control apparatus of the access control device and/or the control apparatus of the laboratory instrument is configured to store at least one, some or all booking data records, entered by at least one user, in the storage apparatus.

Preferably, the control apparatus of the access control device and/or the control apparatus of the laboratory instrument is embodied to evaluate some or all booking data records, entered by at least one user and stored in the storage apparatus, in accordance with an evaluation method stored in the storage apparatus and to create the schedule according to at least one criterion by virtue of the booking data records being sorted in accordance with the at least one criterion of a sort method stored in the control apparatus.

Preferably, the control apparatus of the access control device and/or the control apparatus of the laboratory instrument is embodied to assign the at least one booking data record a priority by means of an evaluation method, which priority is established in accordance with at least one criterion.

The criteria can, in particular, be represented by a data table stored in the control apparatus, in which data table e.g. the priority is related to at least one other parameter, wherein this other parameter may characterize e.g. the user or a user group, or the classification of a treatment in accordance to a list of relevance (e.g. from important to unimportant, expensive to cost-effective, etc.).

Preferably, the control apparatus of the access control device and/or the control apparatus of the laboratory instrument is embodied in such a way that the sort method sorts at least two booking data records in accordance with at least one criterion in order, in particular, to create a schedule which uses other time data than what is provided for in the booking data records of the users.

The criterion can be selected in accordance with the definitions in the evaluation method. Preferably, in order to realize a preferred criterion, the control apparatus is embodied to sort the booking data records under the aspect of a resource being optimized.

By way of example, the resource can be the time; in particular, a minimization of the waiting times can be sought after, a user in each case experiencing said waiting times as the difference between the start time, as desired by said user, and the start time, assigned by the laboratory instrument after evaluation and sort, for the experiment of said user, i.e. the treatment desired by said user. The minimization of the passive time, during which a laboratory instrument is not used, may also be sought after. In particular, it is also possible to plan intermediate servicing, cleaning and/or sterilization procedures, during which e.g. at least one workspace of at least one laboratory instrument or laboratory machine is prepared, in particular prepared manually and/or automatically, and/or cleaned and/or sterilized.

The resource may also be the energy which, as a function of the sequence of treatments, is possibly consumed to a different extent over different and successive ones of said treatments.

The resource may be a consumable, in particular a substance, e.g. a cleaner, or specific transport containers, e.g. pipette tips, or storage containers, e.g. microtiter plates, which, as a function of the sequence of treatments, are consumed to a different extent over various and successively carried out ones of said treatments. The same processes are possibly used in treatments planned by different users, and so it may be efficient to sort bookings on the basis of the processes. By way of example, it is conceivable that a specific substance and/or a specific consumable and/or a specific tool is used in a plurality of processes planned by different (or the same) user(s). Then, it may be particularly efficient to store this substance or this consumable or this tool in the laboratory instrument such that some transport processes become superfluous, as a result of which time and, optionally, the resource itself are saved, which resources often need to be stored under sterile conditions. By way of example, it would also be possible for two treatments, provided temporally in succession in the booking schedule, to be able to share specific consumables. By way of example, one and the same storage container could be used in both treatments, and therefore it is efficient to use the storage container for the second treatment after completion of the first treatment instead of disposing of the first storage container at the end of the first treatment and using a further storage container at the beginning of the second treatment. As a result, it is possible to save material and time in many situations.

The resource can also be the plurality of laboratory instruments, on which the bookings occurring during a booking period of time are to be distributed automatically in accordance with the plurality of booking data records from a plurality of users in order to obtain an optimal use of the parks of laboratory instruments available in a laboratory. In particular, there may be experiments which require the synchronized use of more than one laboratory instrument. The resource may therefore consist of using a plurality of laboratory instruments optimally in time, in particular taking into account at least one experiment or a plurality of experiments which may each require different laboratory instruments.

By way of example, it is possible that a higher ranked role, e.g. an "administrator", is able to delete or move the bookings of treatment apparatuses, i.e. booking entries in the booking schedule, for example because an (external) service technician wishes/needs to service the treatment apparatus (es) on said date or because of other aforementioned reasons. Particularly from the view of the customer, an action without consultation is not preferred, rather a note to the user(s) of the booked one or more treatment apparatuses to the effect that the use of the treatment apparatus needs to be moved to a later date is preferable. In this context, proposing a suitable alternative time may also be expedient. The control apparatus is preferably embodied to emit such a notification via the user interface apparatus of the relevant user, in particular by using a remote data connection.

To the extent that a treatment apparatus is in strong demand, a booking mechanism, which is designed as a FIFO list (FIFO—first in, first out) and which in turn is used for informing the top-most user the moment the treatment apparatus becomes unoccupied or when it will be unoccupied during a selected period of time in the future, is particularly suitable. This information then preferably also comprises the timeframe for which the treatment apparatus is available. The topmost user would then receive the priority to occupy the treatment apparatus for a defined period of time. If he does not do this, the user is removed from the list and the option for occupation is transferred to the next user on the list, etc.

The term "instrument-controlled treatment" means that the treatment of the at least one laboratory sample is at least partly controlled, in particular performed, by the laboratory instrument. To the extent that the treatment is controlled and/or carried out by the laboratory instrument, said treatment in this respect is, in particular, not controlled and/or performed by the user, in particular not controlled and/or performed manually by the user.

An instrument-controlled treatment is furthermore preferably understood to mean that the treatment is at least partly controlled, in particular performed, by the laboratory instrument as a function of at least one user input. The user input may occur prior to the start of the treatment and/or during the treatment. The user input preferably occurs using a user interface apparatus, which is preferably a component of the laboratory instrument or which is provided separately from the laboratory instrument and signal connected to the control apparatus of the laboratory instrument and/or to the control apparatus of the access control device. The user input serves, in particular, for entering at least one parameter, the value of which influences and/or controls the treatment. This parameter can, in particular, be a program parameter.

The "instrument-controlled treatment" denotes, in particular, the at least partly automated treatment. In the case of a partly automated treatment, it is possible, in particular, for the treatment to be performed in such a way that, after the treatment has started and before the treatment is complete, there is at least one user input, by means of which the user can influence the current treatment, in particular by virtue of said user e.g. responding to an automatic query brought about by means of a user interface apparatus of the laboratory instrument, in particular by virtue of confirming or denying an input or undertaking other inputs. In the case of the partly automated treatment, it is possible, in particular, for the treatment to have a plurality of treatment steps which, in particular, are performed automatically and successively in time and which have at least one treatment step that requires a user input, which, in particular, is brought about via a user interface apparatus.

An instrument-controlled treatment is preferably a program-controlled treatment, i.e. a treatment controlled by a program. A program-controlled treatment of a sample should be understood to mean that the process of treatment substantially takes place by working through a plurality or multiplicity of program steps. Preferably, the program-controlled treatment takes place using at least one program parameter, in particular at least one program parameter selected by the user. A parameter selected by a user is also referred to as a user parameter. The program-controlled treatment preferably takes place with the aid of a digital data processing apparatus which, in particular, may be a component of the control apparatus of the laboratory instrument. The data processing apparatus can comprise at least one processor, i.e. a CPU, and/or at least one microprocessor. The program-controlled treatment is preferably controlled and/or performed in accordance with the prescriptions of a program, in particular a control program. In particular, substantially no user activity is required in the case of a program-controlled treatment, at least after acquisition of the program parameters required from the user.

A program parameter is understood to mean a variable which can be set in a predetermined manner within a program or sub-program and is valid for at least one execution (call) of the program or sub-program. The program parameter is set, e.g. by the user, and controls the program or sub-program and causes a data output as a function of this program parameter. In particular, the program parameter influences and/or controls the control of the instrument, and/or the data output by the program control said instrument, in particular the control of the treatment by means of the at least one treatment apparatus.

A program parameter may be a program parameter required on the part of the user. A program parameter required on the part of the user is distinguished by the fact that it is required for performing a treatment, in particular for performing a process program. Other program parameters, which are not required on the part of the user, may be derived from the program parameters required on the part of the user or may be made available in a different manner, in particular they may optionally be set by the user. In particular, a program parameter is set by a user by displaying a selection of possible predetermined values from a list of predetermined values stored in the laboratory instrument, wherein the user selects, and therefore sets, the desired parameter from this list. It is also possible for this program parameter to be set by virtue of the user entering the value, e.g. by virtue of entering a numeric number corresponding to the desired value by means of a numeric pad or by virtue of said user increasing or reducing a value continuously or in increments until said value corresponds to the desired value and the value is set thus. Other forms of entry, e.g. by voice and/or gesture control, are conceivable.

A program is, in particular, understood to mean a computer program. A program is a sequence of statements, in particular consisting of declarations and instructions, enabling a specific functionality, object or problem to be handled and/or solved on a digital data processing system. A program is generally available as software which is used with a digital data processing system. In particular, the program can be available as firmware, in particular as firmware of the control apparatus of the laboratory instrument and/or of the access control device in the case of the present invention. The program is usually available as a program file, often in the form of so-called machine code, which can be executed on a data medium, which program file is loaded into the main memory of the computer of the digital data processing system for execution purposes. The program is processed and therefore executed by the processor(s) of the computer as a sequence of machine commands, i.e. processor commands. In particular, a "computer program" is also understood to mean the source text of the program from which the executable code can be generated in the progress of the control of the laboratory instrument.

As is conventional, a statement denotes a central element of a programming language. Programs of such languages are primarily composed of one or more statements. A statement constitutes a single prescription, formulated within the syntax of a programming language, which prescription is to be executed when working through the program. The syntax of a statement is set by the respective programming language or the specification thereof. In machine-oriented programming, statements are often also referred to as commands.

Statements are usually assignments, control statements (such as branches, loops and conditional statements) and procedural calls. Assertions, declarations, class definitions and function definitions and also (?) statements are in part dependent on the programming language. Thus, the statements of the control program can be configured in a conventional manner.

As is conventional, a program module is understood to be a complete functional unit of software, consisting of a sequence of processing steps and data structures. Here, in particular, the following definitions may apply: the content of a module is often a recurring calculation or handling of data, which needs to be carried out a number of times. Modules offer an encapsulation by separating interface and implementation: the interface of a module defines the data elements which, as input and result of the processing, are required by the module. The implementation contains the actual program code. By way of example, a module is called as a function or sub-program, executes a number of processing steps and, as a result, provides data back to the calling program. A module itself is able to call further modules—thus, a hierarchy of program calls is possible. The data structures and processes set in modules can, when necessary, be inherited and inherited by other modules. Therefore, modules are an essential element in structured and object-oriented programming.

A control program is understood to mean an executable computer program, which preferably controls and/or performs the desired treatment of the at least one sample, in particular as a function of at least one program parameter. This program parameter can be a program parameter influenced and/or set by the user. In particular, the treatment can be controlled by virtue of the control apparatus generating one or more control parameters as a function of the program parameters, by means of which control parameters the at least one treatment apparatus is controlled. The laboratory instrument preferably has an operating system, which can be or comprise a control program. In particular, the control program can denote an operating system of the laboratory instrument or a component of the operating system. The operating system controls the treatment and further operating functions of the laboratory instrument.

In particular, the control program can be signal connected to the access control device and/or can control the access control device. The control apparatus of the access control device can be integrated into the control apparatus of the laboratory instrument or can be embodied separately from this control apparatus. The access control device can be integrated into the control apparatus of the laboratory instrument. The control device of the access control device can be integrated into control device of the laboratory instrument, can be controllable by the control program and/or can, in particular, be integrated into the control program. The control program can control further preferably provided functions of the laboratory instrument, for example an energy-saving function of the laboratory instrument or a communication function for communication with external data processing apparatuses which, in particular, are provided separately from the laboratory instrument and, in particular, are not a component of the laboratory instrument.

A process program is understood to mean a program which determines the specific progress of a treatment, in particular in accordance with a predetermined type of treatment and/or in accordance with a manner set on the part of the user.

The invention furthermore relates to a laboratory instrument for instrument-controlled treatment of at least one laboratory sample, which laboratory instrument comprises at least one treatment apparatus for performing the treatment of the at least one laboratory sample, and an access control device according to the invention.

Preferably, the laboratory instrument comprises a communication apparatus for establishing a remote data connection for data interchange with an external instrument, which likewise comprises a suitable communication apparatus for establishing a remote connection for data interchange with the laboratory machine. Such a communication apparatus can be embodied for establishing a radio connection, in particular a mobile communications connection. The communication apparatus is preferably configured to enable remote access of the user to the laboratory instrument, in particular for selecting or setting of at least one parameter, in particular a parameter which controls a function of the laboratory instrument, in particular the function of performing a treatment.

Preferably, the control apparatus of the access control device or of the laboratory instrument is embodied to provide synchronization data. Preferably, the access control device, in particular the control apparatus of the access control device, is configured in such a way that, if at least one condition is satisfied, information about the operating state of the laboratory instrument, measured values or settings and programs of the laboratory instrument which can be influenced by the user are transmitted to the second user interface apparatus via the interface apparatus. As a result of this information transfer, the laboratory instrument, in particular a treatment running thereon, can continue to be observed and/or controlled by means of the second user interface apparatus. In particular, the use state of the first interface apparatus can be partly or completely copied or cloned in the second user interface apparatus. The information transfer can, in particular, be a synchronization process. The first and second user interface can be synchronized, in particular in this manner. The at least one condition may be that the access of the accessing user is brought about by means of a remote data connection via a (mobile) user interface apparatus and the request of the user is brought about after synchronization. The at least one condition can moreover be the condition a) or b), namely the response to the check whether the logging-on user has already previously, via a first user interface apparatus, a) activated one or more currently executed functions of the laboratory instrument or b) logged on. In cases a) and b), the synchronization would only be allowed for a user with an active session and/or with currently activated functions on the laboratory instrument, in particular with running treatments which were initiated by the user. However, it is also possible and preferred for a further user to be allowed to carry out synchronization, e.g. in order to perform remote control for the purpose of providing assistance during the current session or treatment or for the purpose of carrying out servicing works, etc.

Preferably, the control apparatus of the access control device is configured to transfer these synchronization data to an—in particular mobile—user interface apparatus. Preferably, these synchronization data are suitable for displaying the information displayed in the display of the user interface apparatus at least partly in an identical manner on the display of the—in particular mobile—user interface apparatus.

The term laboratory instrument denotes, in particular, an instrument which is embodied for instrument-controlled treatment of at least one laboratory sample and which is embodied for use in a laboratory. This laboratory can be, in particular, a chemical, biological, biochemical, medical or forensic laboratory. Such laboratories serve for research and/or analysing laboratory samples, but can also serve for the manufacture of products by means of laboratory samples or the manufacture of laboratory samples.

A laboratory instrument is preferably one of the following laboratory instruments and/or is preferably embodied as at least one of the following laboratory instruments: a laboratory centrifuge, also referred to as "centrifuge" within the scope of the description of the present invention; a thermocycler, also referred to as "cycler" within the scope of the description of the present invention; a laboratory spectral photometer, also referred to as "biospectrometer" within the scope of the description of the present invention; a cell counting instrument, also referred to as "cell counter" within the scope of the description of the present invention, in particular optical counting instruments; a laboratory incubator, also referred to as "incubator" within the scope of the description of the present invention; a laboratory shaker, also referred to as "shaker" within the scope of the description of the present invention; a laboratory mixer, also referred to as "mixing device"; a laboratory freezer, also referred to as "freezer" within the scope of the description of the present invention; a bioreactor, also referred to as fermenter within the scope of the description of the present invention; a safety work bench, in particular biological safety cabinet, also referred to as "biosafety cabinet" within the scope of the description of the present invention; a sample plate reader, also referred to as "plate reader" within the scope of the description of the present invention, in particular "microplate reader"; a laboratory machine for treating fluid samples, in particular a pipetting machine.

A laboratory centrifuge is an instrument which works using inertia. The laboratory centrifuge, in particular the treatment apparatus of the laboratory centrifuge, comprises, in particular, at least one rotor, in which the at least one laboratory sample can be disposed. The at least one rotor is disposed rotatably in at least one centrifuge vessel. The laboratory centrifuge, in particular the treatment apparatus of the laboratory centrifuge, comprises at least one drive apparatus, by means of which the rotation is driven and/or braked. The samples can be disposed in the at least one rotor, preferably in laboratory containers, e.g. sample tubules, which are disposed in suitable holders in the rotor. The laboratory centrifuge, in particular the treatment apparatus of the laboratory centrifuge, preferably comprises at least one heater/cooling apparatus, by means of which the temperature of the at least one sample disposed in the rotor can be controlled and/or regulated. The laboratory centrifuge, in particular the treatment apparatus of the laboratory centrifuge, preferably comprises a timer apparatus, by means of which time parameters of the rotation or temperature settings can be controlled. The functionality is based upon the centrifugal force, which occurs due to a uniform circular motion of the samples to be centrifuged. The centrifugal force is used for substance separation of substances with different densities, which are contained in a sample. A centrifuge can perform a separation method, in which, in particular, the constituents of suspensions, emulsions and/or gas mixtures are separated. The instrument-controlled treatment of the at least one laboratory sample corresponds to a rotational treatment in a laboratory centrifuge, with at least one sample being subjected to said rotational treatment. Possible parameters, in particular program parameters, in particular user parameters, which are used to influence a rotational treatment, define, in particular, a temperature of the laboratory centrifuge, a rotational speed of the laboratory centrifuge, a time parameter of the rotation or a temperature setting and/or at least one progress parameter, which influences or defines the progress, in particular the sequence, of a rotation program consisting of a plurality of rotation steps. The temperature of the laboratory centrifuge can, in particular, be at least one temperature in the interior of the at least one rotor, in particular at least one temperature of at least one sample.

A thermocycler is an instrument that is able, successively in time, to set the temperature of at least one sample to a predetermined temperature and to keep said sample at this temperature level for a predetermined duration. The progress of this temperature control is cyclical. That is to say, a predetermined temperature cycle, i.e. a sequence of at least two temperature levels, is carried out repeatedly. This method serves, in particular, for performing a polymerase chain reaction (PCR). In this context, a thermocycler is sometimes also referred to as a PCR block. A thermocycler, in particular the treatment apparatus of the thermocycler, preferably has a thermoblock. A thermoblock is a sample holder made of a heat-conducting material, usually a metal-containing material or a metal, in particular aluminium or silver. The sample holder comprises a contacting side which is contacted by at least one heater/cooling apparatus of the thermocycler, in particular by a Peltier element. The thermocycler, in particular the treatment apparatus of the thermocycler, comprises a regulation apparatus with at least one control loop, to which the at least one heater/cooling apparatus is assigned as an actuator and at least one temperature measurement apparatus is assigned as a measurement member. The temperature is regulated to a temperature level by means of the controlling system. A cooling body of the thermocycler, in particular of the treatment apparatus of the thermocycler, serves for cooling sections of the thermocycler, in particular for cooling the Peltier elements. The thermocycler, in particular the treatment apparatus of the thermocycler, may comprise further heater and/or cooling elements. The thermocycler, in particular the treatment apparatus of the thermocycler, preferably comprises a timer apparatus, by means of which time parameters for setting the temperature cycle can be controlled. The instrument-controlled treatment of the at least one laboratory sample corresponds to a temperature cycle treatment in a thermocycler, with at least one sample being subjected to said rotational treatment. Possible parameters, in particular program parameters, in particular user parameters, which are used to influence a temperature cycle treatment, define, in particular, the temperature of the temperature level, the duration of a temperature level, the control of further heater and/or cooling elements and/or the number of temperature levels or cycles and/or at least one progress parameter, which influences or defines the progress, in particular the sequence, of a temperature monitoring program consisting of a plurality of steps.

A laboratory spectrophotometer is an instrument which, by illuminating at least one measurement volume of at least one laboratory sample, usually over the whole spectrum of visible light from infrared to ultraviolet, establishes the values of diffuse reflection. Diffuse reflection refers to the situation in which a measurement volume absorbs part of the light spectrum and transmits part of the spectrum (transparent media) or reflects it (opaque media). The laboratory spectrophotometer is used, in particular, to measure the absorptivity of a sample as a function of the light wavelength. Moreover, it is possible, in particular, to extend the field of application of the laboratory spectrophotometer by means of various modules. By way of example, it is conceivable to dispose a fluorescence module for measuring fluorescence or a temperature-control module for controlling the temperature of the sample in the spectrometer. The measured absorption spectrum contains, in particular, the light intensities measured at specific wavelengths. The absorption spectrum is typical of the laboratory sample or the substance contained therein or the substances. This can be used for qualitative analysis of the laboratory sample. If the liquid sample or the substance dissolved therein is known, the concentration of the dissolved substance can be established by measuring the absorption. This can be used for quantitative analysis of the laboratory sample. The laboratory spectrophotometer, in particular the treatment apparatus of the laboratory spectrophotometer, preferably comprises at least one light source, preferably at least one timer, preferably at least one photodetector. The instrument-controlled treatment of the at least one laboratory sample corresponds to a light and measurement treatment in a laboratory spectrophotometer, with at least one sample being subjected to said treatment. Possible parameters, in particular program parameters, in particular user parameters, which are used to influence a light and measurement treatment, define, in particular, the optical light spectrum, by means of which the at least one sample is irradiated and/or at least one progress parameter, which influences or defines the progress, in particular the sequence, of a light and measurement treatment program consisting of a plurality of steps.

A cell counting instrument serves for counting biological cells or particles which are contained in the laboratory sample. There are different physical principles which can be used to count cells, in particular optical methods, in which the laboratory sample to be measured is disposed in a counting chamber, there is additional illumination, particularly in the case of automatically operating ones, and an image of the cells or particles disposed in the counting chamber is acquired and evaluated. A further established method lies in measuring the impedance: a cell counting instrument embodied as a Coulter counter guides the laboratory sample containing the cells through an aperture ("measurement port"). Each passage of a cell through the aperture is detected electrically as a countable event. Optical cell counting instruments, in particular the treatment apparatus of the cell counting instrument, preferably comprise, depending on the embodiment, at least one light source, at least one image acquisition unit and at least one image evaluation unit, and additionally, inter alia, a positioning apparatus. The instrument-controlled treatment of the at least one laboratory sample corresponds e.g. to a light and measurement treatment in the case of an optical cell counting instrument, a pumping and measurement treatment in the case of an instrument operating according to the Coulter principle, to which treatment the at least one sample is subjected. Possible parameters, in particular program parameters, in particular user parameters, which are used to influence a light and measurement treatment or the pumping and measurement treatment, define, in particular, the light intensity of the light source, by means of which the at least one sample is irradiated and/or at least one progress parameter, which influences or defines the progress, in particular the sequence, of a light and measurement treatment program or the pumping and measurement treatment program consisting of a plurality of steps. Moreover, in the case of optical counting instruments, the algorithms necessary for the image evaluation, the sequence and parameterization thereof are decisive for the significance of the measurement result. Optical measurement instruments, but also Coulter counters, often use counting chambers for single use ("consumables"); these are plastic articles in the style of conventional Neubauer counting chambers or, in the case of Coulter counters, "lab-on-a-chip"-like disposable counting chambers. However, there are also instruments which operate without these consumables (e.g. "CASY").

A laboratory incubator is an instrument by means of which controlled climatic conditions for various biological development and growth processes can be set up and maintained. It serves to set up and maintain a microclimate with regulated gas and/or humidity and/or temperature conditions in an incubator space, wherein this treatment may be dependent on time. The laboratory incubator, in particular the treatment apparatus of the laboratory incubator, comprises, in particular, a timer, in particular a timer switch, a heater/cooling apparatus and preferably a setting for regulating the substitute gas supplied to the incubator space, in particular fresh air, a setting apparatus for the composition of the gas in the incubator space of the laboratory incubator, in particular for setting the $CO_2$ and/or $O_2$ content of the gas and/or a setting apparatus for setting the humidity in the incubator space of the laboratory incubator. The laboratory incubator, in particular the treatment apparatus of the laboratory incubator, comprises, in particular, the incubator space, furthermore preferably a regulation apparatus with at least one control loop, to which at least one heater/cooling apparatus is assigned as an actuator and at least one temperature measurement apparatus is assigned as a measurement member. The temperature can be regulated in the incubator by means of the controlling system. $CO_2$ incubators serve, in particular, for cultivating animal or human cells. Incubators may have turning devices for turning the at least one laboratory sample and/or a shaker apparatus for shaking or moving the at least one laboratory sample. The instrument-controlled treatment of the at least one laboratory sample corresponds to a climate treatment in a laboratory incubator, with at least one sample being subjected to said treatment. Possible parameters, in particular program parameters, in particular user parameters, which are used to influence a climate treatment, define, in particular, the temperature of the incubator space, in which the at least one sample is incubated, the $O_2$ and/or $CO_2$ partial pressure in the incubator interior, the humidity in the incubator interior and/or at least one progress parameter, which influences or defines the progress, in particular the sequence, of a incubation treatment program consisting of a plurality of steps.

A laboratory shaker serves for moving a laboratory sample, in particular for mixing a laboratory sample comprising a plurality of constituents. There are different embodiments of laboratory shakers, in particular overhead shakers or flatbed shakers. Laboratory shakers can comprise a temperature control function for controlling the temperature of at least one laboratory sample and can, in particular, comprise an incubator function for incubating the at least one laboratory sample in controlled climatic conditions. Laboratory shakers, in particular the treatment apparatus thereof, can, in particular, be configured to perform an oscillating motion. Laboratory shakers, in particular the treatment apparatus thereof, comprise, in particular, a drive for driving the motion, comprise, in particular, a timer apparatus, by means of which time parameters of the setting of the shaker treatment can be controlled and, in particular, comprise at least one heater/cooling apparatus and at least one control apparatus with at least one control loop, which is assigned the at least one heater/cooling apparatus as actuator and at least one temperature measurement apparatus as measurement member. The instrument-controlled treatment of the at least one laboratory sample corresponds to a shaker treatment in a laboratory shaker, with at least one sample being subjected to said treatment. Possible parameters, in particular program parameters, in particular user parameters, which are used to influence a shaker treatment, define, in particular, the movement intensity, in particular the movement frequency in the case of an oscillating drive, a time period during the shaker treatment and/or at least one progress parameter, which influences or defines the progress, in particular the sequence, of a shaker treatment program consisting of a plurality of steps.

A laboratory mixer, also referred to as "mixing device", serves like the laboratory shaker for moving a laboratory sample, in particular for mixing a laboratory sample comprising a plurality of constituents. Compared to a laboratory shaker, a laboratory mixer enables movements with higher frequencies, in particular with higher rotational speeds. Laboratory mixers, in particular the treatment apparatus thereof, can, in particular, be configured to perform an oscillating motion. Laboratory mixers, in particular the treatment apparatus thereof, comprise, in particular, a drive for driving the motion, comprise, in particular, a timer apparatus, by means of which time parameters of the setting of the mixer treatment can be controlled and, in particular, comprise at least one heater/cooling apparatus and at least one control apparatus with at least one control loop, which is assigned the at least one heater/cooling apparatus as actuator and at least one temperature measurement apparatus as measurement member. The instrument-controlled treatment of the at least one laboratory sample corresponds to a mixer treatment in a laboratory mixer, with at least one sample being subjected to said treatment. Possible parameters, in particular program parameters, in particular user parameters, which are used to influence a mixer treatment, define, in particular, the movement intensity, in particular the movement frequency in the case of an oscillating drive, a time period during the mixer treatment and/or at least one progress parameter, which influences or defines the progress, in particular the sequence, of a mixer treatment program consisting of a plurality of steps.

A laboratory freezer serves for storing at least one laboratory sample in a freezer room at regulated temperatures, in particular in the freezer range from $-18°$ C. to $-50°$ C. or in the ultra-freezer range from $-50°$ C. to $-90°$ C. In particular, a laboratory freezer is not a refrigerator, which can be used for cooling at temperatures in the range from $0°$ C. to $10°$ C. or from $-10°$ to $10°$ C. in particular. The laboratory freezer, in particular the treatment apparatus of the laboratory freezer, comprises, in particular, at least one cooling apparatus and at least one regulation apparatus with at least one control loop, to which at least one cooling apparatus is assigned as an actuator and at least one temperature measurement apparatus is assigned as a measurement member. A laboratory freezer, in particular the treatment apparatus of the laboratory freezer, comprises, in particular, a monitoring measurement instrument for measuring the temperature and/or in particular at least one alarm apparatus, by means of which an alarm signal is emitted if the temperature measured in the freezer space departs from a permitted temperature range. A laboratory freezer, in particular the treatment apparatus of the laboratory freezer, can, in particular, comprise an information reader for reading information. This information can be contained in an information medium which can be connected to an article. This article can, in particular, be a sample container which can contain at least one laboratory sample. The information medium can, in particular, comprise an RFID chip or other identification features, such as e.g. a barcode, a data matrix code, a QR code, which can be read by suitable methods. The instrument-controlled treatment of the at least one laboratory sample corresponds to a low-temperature treatment in a laboratory freezer, with at least one sample being subjected to said treatment. Possible parameters, in particular program parameters, in particular user parameters, which are used to influence a low-temperature treatment, define, in particular, the temperature of the freezer-space space, in which the at least one sample is frozen and/or the information read process, which is preferably carried out when an article provided with an information medium is transferred from a user into the laboratory freezer.

A bioreactor comprises a container, in which specific micro-organisms, cells or small plants are cultivated (also: fermented) under conditions which are as ideal as possible. The operation of a bioreactor therefore is an application of biotechnology, which, in technical apparatuses, uses biological processes, in particular bioconversion or biocatalysis, or makes these available. Factors which can be controlled or monitored in most bioreactors, in particular by setting appropriate parameters, are the composition of the nutrient solution, the oxygen supply, temperature, pH, sterility and/or other factors. The purpose of cultivation in a bioreactor may be the harvesting of cells or constituents of cells, or the harvesting of metabolic products. By way of example, these can be used as an active ingredient in the pharmaceutical industry or as a basic chemical in the chemical industry. The breakdown of chemical compounds may also take place in bioreactors, such as e.g. in sewage water treatment in sewage works. The production of beer, wine and other such products likewise occurs in bioreactors. The most diverse type of organisms are cultivated in bioreactors for various purposes. A bioreactor can therefore have different configurations. It can be configured as stirred tank reactor, which can have a volume from a few millilitres to hundreds of litres and can be filled with nutrient solution. It can also be used or embodied as a fixed bed reactor or photobioreactor. A bioreactor can be part of a bioreactor system, preferably of a parallel bioreactor system. In such a parallel bioreactor system, a multiplicity of bioreactors are operated in parallel and controlled with high precision. A bioreactor, in particular the treatment apparatus thereof, comprises, in particular, a stirring apparatus for stirring the sample contained in the reactor container, in particular for stirring the nutrient solution. A bioreactor, in particular the treatment apparatus thereof, comprises, in particular, a pump apparatus for pumping the laboratory sample, which is preferably configured as nutrient solution. A bioreactor, in particular the treatment apparatus thereof, comprises, in particular, a setting apparatus for setting a gas content in the reactor container, in particular the content of $CO_2$ and/or $O_2$ or of dissolved oxygen (DO). A bioreactor, in particular the treatment apparatus thereof, comprises, in particular, a setting apparatus for setting, in particular regulating, a pH in the sample in the reactor container. The instrument-controlled treatment of the at least one laboratory sample corresponds to, in particular, a nutrient solution treatment in a bioreactor, with at least one sample, preferably embodied as nutrient solution, being subjected to said treatment. Possible parameters, in particular program parameters, in particular user parameters, which are used to influence a nutrient solution treatment, define, in particular, the temperature of the nutrient solution in the reactor container and/or the speed of the stirrer apparatus, in particular the rotational speed and/or the pump speed or the metering speed and/or a gas content in the nutrient solution, in particular $CO_2$ and/or $O_2$ or dissolved oxygen (DO) and/or the pH value of the nutrient solution and/or at least one progress parameter, which influences or defines the progress, in particular the sequence, of a nutrient solution treatment program consisting of a plurality of steps.

A biological safety cabinet serves, in particular, for secure storage or stockpiling of hazardous materials, in particular for meeting a biological protection level. In particular, these levels are standardized in EU Directive 2000/54/EG on the protection of workers from risks related to exposure to biological agents at work and, in Germany, in the German Ordinance on Biological Substances. A biological safety cabinet is intended to prevent laboratory samples stored in a biological safety cabinet from endangering the surroundings if danger develops. In particular, safety is ensured by virtue of the atmosphere contained in the receiving region of the biological safety cabinet being replaced and, in particular, filtered. Here, in particular, this atmosphere is conveyed through the receiving region by a conveying apparatus and moved through a filter, which filters the atmosphere and, in particular, removes hazardous materials. The biological safety cabinet, in particular the treatment apparatus thereof, comprises, in particular, a conveying apparatus for conveying atmospheric gas, comprises, in particular, a timer apparatus for measuring a filter operation duration and a ventilator operation duration and/or comprises, in particular, a measurement apparatus for measuring a conveyed amount of atmospheric gas. The instrument-controlled treatment of the at least one laboratory sample corresponds, in particular, to an atmospheric gas treatment for treating the atmospheric gas, in which the at least one sample is stored, in a biological safety cabinet. Possible parameters, in particular program parameters, in particular user parameters, which are used to influence an atmospheric gas treatment, define, in particular, the temperature of the atmospheric gas in the receiving region and/or the flow speed of the atmospheric gas conveyed by the conveying apparatus, the amount of air conveyed, the filter operation duration and/or the ventilator operation duration.

A sample plate reader, also referred to as "plate reader" or "microplate reader", is a laboratory instrument for detecting biological, chemical or physical events of samples in microtitre plates. They are used widely in research: for active ingredient research, bioassay validation, quality control and manufacturing processes in the pharmaceutical and biotech industry and in academic organizations. The sample plate reader can, in particular, comprise at least one light source or radiation source, can comprise at least one photodetector, can comprise a temperature control apparatus for the temperature control of the samples or the sample plates and can comprise a timer. Sample reactions can be tested in 6-1536 well microtiter plates. The most common format for sample plates, in particular microtiter plates, which are used in academic research laboratories or in clinical-diagnostic laboratories, is a 96 well plate (an 8 by 12 matrix) with a typical individual volume of between 100 and 200 µl per well. microtiter plates with a higher density (384 or 1536 well microtiter plates) are typically used in screening applications if the throughput (number of samples to be processed per day) and assay costs per sample become critical parameters, and these have a typical assay volume of between 5 and 50 µl per well. The treatment is, in particular, an optical measurement of the microtiter plate, in particular the measurement of an absorption, fluorescence intensity, luminescence, time-resolved fluorescence and/or fluorescence polarization. Possible parameters, in particular program parameters, in particular user parameters, which are used to influence a measurement, define, for example, the intensity of the light source, the sensitivity of the photodetector, a time duration and/or a temperature.

A laboratory machine for treating fluid samples, in particular an automatic pipette, serves for the program-controlled treatment of these samples. A laboratory machine can be a laboratory instrument or comprise at least one laboratory instrument of the aforementioned type and/or can be embodied to carry out at least one, some or all of the treatments that can be executed by this aforementioned laboratory instrument. A laboratory machine comprises the treatment apparatus for automatic, program-controlled treatment of the at least one laboratory sample, wherein the treatment is controlled by using a plurality of program parameters, which are at least partly selected by the user. In the process, the sample can, for example, be moved and/or transported by the laboratory machine or a treatment apparatus of the laboratory machine. The movement can be brought about by transport in movable sample containers or by guidance through tube systems, capillaries or pipette tips. Here, liquid samples are, in particular, transported by suction, i.e. by pipetting, or, more generally, by the application of pressure differences. By way of example, a sample can be divided or diluted by a treatment of the sample. The contents of a sample can be analysed or it is possible, e.g. by way of a chemical reaction, for new contents to be produced, in particular by using the sample. In the context of, in particular, handling and analysing DNA or RNA or the constituents thereof, laboratory machines aid in obtaining a wealth of information within a suitable period of time or in analysing many such samples. This treatment apparatus of a laboratory machine usually comprises a worktop with workstations, on which samples can be handled or stored in various ways. For the purposes of transporting e.g. liquid samples between various positions, in particular sample containers, the treatment apparatus usually comprises an instrument-controlled movement device and an instrument-controlled fluid-transfer apparatus, which can e.g. comprise a pipetting system. Both the transport of the samples and the treatment thereof at the various stations can be carried out in an instrument-controlled manner, in particular in a program-controlled manner. Then the treatment is preferably at least partly or completely automated.

The user of the laboratory machine can preferably set the type of treatment for the sample. Such a treatment type may, in particular, serve for:

nucleic acid purification, in particular:
    "MagSep Blood gDNA": purification of genomic DNA from whole blood, in particular using the Eppendorf® MagSep Blood gDNA kit;
    "MagSep Tissue gDNA": purification of genomic DNA from living tissue, in particular using the Eppendorf® MagSep Tissue gDNA kit;
    "MagSep Viral DANN/RNA": purification of viral RNA or DNA from cell-free bodily fluids, in particular using the Eppendorf® MagSep Viral DNA/RNA kit;
and PCR applications, in particular:
    "Compose Mastermix";
    "Normalize Concentrations";
    "Create Dilution Series";
    "Setup Reactions".

A laboratory instrument, in particular the laboratory machine, is preferably embodied in such a way that the treatment of the at least one laboratory sample can be controlled automatically using the acquired program parameters. A laboratory instrument, in particular the laboratory machine, in particular the control program thereof, is preferably embodied in such a way that the input undertaken by the user, in particular the at least one value of at least one program parameter, can be used, where necessary, to automatically establish further required program parameters, in particular by calculation or comparison with data in a database of the laboratory machine. In particular, the control parameters preferably used for performing the treatment in detail are preferably determined automatically. As a result of these measures, the operation of the laboratory instrument becomes more convenient, the user is spared from, in particular, designing a program code since these steps are carried out, in particular automatically, by the laboratory instrument. In a preferred embodiment of the invention, all that is required from the user are the entries which are directly related to the treatment of the samples to be performed. Often, these are the same specifications that would also be necessary for performing the treatment manually and these are known to the user. By contrast, the parameters which relate to the control of the laboratory instrument, in particular the control parameters, need not be set in detail since these are preferably set automatically. Control parameters are the parameters required in detail for controlling the technical constituents of the treatment apparatus. Control parameters can be program parameters or can be parameters derived therefrom for the technical implementation, in particular automatically determined parameters.

Preferably, a laboratory instrument, in particular the laboratory machine, automatically selects the fitting set of program parameters following the treatment type selection by the user, wherein the program parameters thereof required on part of the user are then queried from the user in steps (b) and (c). The set of program parameters can contain, firstly, the program parameters required on part of the user and can contain, secondly, further program parameters. These further program parameters can be set automatically depending on the selected treatment of type or can be set automatically depending on at least one or all program parameters entered by the user and/or can be stored in the storage apparatus. The stored parameter sets are preferably optimized for the type of treatment—or become optimized by the laboratory machine—such as that the user preferably requires no specialist knowledge for optimizing the parameters. The control parameters which are necessary for performing the specific treatment by means of the treatment apparatus are derived from the program parameter set.

A program parameter set of program parameters specific to a treatment type is preferably defined for this treatment type. The program parameters of this program parameters set can, in particular, define the accessories to be used for the treatment, e.g. sample container, transport container and/or the further consumables and/or tools to be used.

The mapping between program parameter set and treatment type is stored in the storage apparatus of the laboratory instrument, in particular of the laboratory machine. Preferably, the laboratory instrument is embodied in such a way that the user can store and/or use more such mappings in the laboratory instrument. The operation of the laboratory instrument becomes particularly efficient by these mappings in combination with the clear and well-structured querying of the program parameters. This mapping is preferably brought about by using one or more program modules, wherein a program module is respectively tailored to a specific application:

Preferably, the laboratory instrument, in particular the laboratory machine, comprises at least one program module, with a predetermined program module serving for controlling a predetermined laboratory problem for treating laboratory samples. As a result, the use of the laboratory instrument, in particular of the laboratory machine, becomes even more flexible.

The laboratory instrument, in particular the laboratory machine, can preferably be modified in such a way that it can be used to perform further treatment types. This can be brought about by virtue of the files and/or programs or program constituents required for this, in particular a program module mapped to the treatment type, being subsequently transmitted to the laboratory machine, in particular the storage apparatus thereof.

A laboratory sample is a sample which can be treated in a laboratory. Instead of the term laboratory sample, the term "sample" is also used in the description of the invention. The sample can be a fluid. The sample can be liquid, gel-like, powdery or a solid-state body or comprise such phases. The sample can be a mixture of such phases, in particular a liquid mixture, a solution, a suspension, e.g. a cell suspension, an emulsion or dispersion. A solution is a homogeneous mixture of at least two substances. A liquid sample can be of a type which is usually handled in a biological, chemical or medical laboratory. A liquid sample can be an analysis sample, a reagent, a medium, a buffer etc. A solution has one or more dissolved solid, liquid or gaseous substances (solutes) and furthermore comprises a preferably liquid solvent which, in particular, forms the greater portion or greatest portion of the volume which forms the solution. The solvent may itself be a solution.

The treatment of a laboratory sample or samples, particularly in a laboratory machine, can contain one or more of the processes specified below, in particular simultaneously or in succession:

transport of the laboratory sample, in particular by a transport apparatus, under the action of gravity and/or a force caused by the laboratory machine;

a contactless (non-invasive) physical treatment of the sample, in particular a thermal treatment, in particular heating and/or cooling, in particular a regulated temperature control of the sample; or freezing or defrosting of the sample, or other thermal induction of a phase change of the sample, e.g. evaporating, condensing, etc.; a magnetic treatment of the sample; an optical treatment of the sample, in particular irradiating the sample with radiation, in particular light, in particular visible light, infrared light or UV light, or detection of such radiation, in particular fluorescence light, from this sample; a magnetic treatment of a sample with magnetic constituents, in particular magnetic separation of magnetic constituents, in particular "magnetic beads", from a fluid phase of the sample; moving the sample, i.e. performing a mechanical treatment of the sample, in particular shaking, rotating, oscillating, vibrating, centrifuging, an acoustic treatment, in particular with ultrasound, in each case for e.g. mixing the sample or separating constituents within the sample or for transporting the magnetic constituents out of the sample or into the sample;

invasive physical treatment of the sample, i.e. performing a mechanical treatment of the sample: introducing stirring tools, e.g. stirring bar or magnetic stirrer bar, into the sample and stirring, introducing a probe for acoustic or ultrasonic treatment, introducing transport means, in particular transport containers, into the sample, e.g. dispenser tip or pipette tip or hollow needle or tube; adding other auxiliary means into the sample;

chemical, biochemical or biomedical treatment of the sample: adding chemical (e.g. reactant, reagent, solvent, solute), biochemical (e.g. biochemical macromolecules, e.g. DNA, DNA constituents; pharmaceutical active ingredients) or biomedical (e.g. blood, serum, cell medium) substances;

storing the sample, in particular for a period of time defined in a programme-controlled manner, in particular under specific physical conditions, e.g. at a specific temperature, temperatures or temperature changes, in particular repeated temperature changes, e.g. cyclic and/or periodically repeated temperature changes and/or setting a surrounding pressure, e.g. applying positive pressure or negative pressure, in particular a vacuum, and/or setting a defined surrounding atmosphere, e.g. a protective gas or a specific humidity, under specific radiation conditions, e.g. shielded against visible light, in the dark or under defined irradiation;

measuring or analysing the sample, in particular analysing by means of a non-invasive and/or invasive treatment of the sample, in particular in order to measure at least one or more chemical, physical, biochemical and/or medical properties of the sample, in particular counting of cells by means of a cell counter;

handling of the sample, in particular changing at least one property of the sample, in particular by means of non-invasive and/or invasive treatment of the sample.

This treatment is, in particular, under program control, using at least one program parameter.

In particular, this treatment is brought about in accordance with at least one control parameter which determines the treatment of the laboratory sample by means of the treatment apparatus. A control parameter can set a period of time, a moment in time, a specific sample volume and/or metering volume, a specific sample temperature, etc. A control parameter can relate to the automatic use of a specific transport head, a specific type of transport container, a specific type of sample container, one or more individual samples or of specific positions of these components in the workspace. A control parameter can relate to the treatment of an individual sample or the treatment of a plurality or multiplicity of samples.

A control parameter is preferably selected automatically by the laboratory instrument, in particular the laboratory machine, as a function of at least one program parameter; in particular, it is selected automatically as a function of the program parameters selected by the user. As a result, an advantage for the user is that he does not need to determine all control parameters individually. The user needs no knowledge about the programming of the laboratory instrument. Rather, the control parameters required for the treatment are selected by means of the program parameters entered by the user. As a result, the use of the laboratory instrument is particularly convenient.

A control parameter can also correspond to a program parameter.

The transport of a sample can be transport from a sample container into a transport container and/or from the transport container into a sample container or any other target location. This transport is, in particular, under program control, using at least one program parameter.

The transport container can be e.g. a dispenser container which comprises a movable plunger and an inlet/outlet opening. The plunger generates negative pressure or positive pressure in the dispenser container and thus sucks the sample into the container or re-emits it. This process follows the displacement principle, i.e. the sample to be moved, which is usually liquid and therefore incompressible, is subjected to forced movement by virtue of the volume previously taken up by the sample being moved by the plunger. In general, this plunger is moved, in particular moved under program control, by a movement apparatus which is assigned to the laboratory machine.

The transport container can furthermore be a pipette tip. A pipette tip has an inlet/outlet opening and a second opening. The second opening is coupled to a suction apparatus such that a liquid sample can be sucked (pipetted) from a sample container into the transport container by means of negative pressure. The sample is emitted by ventilating the suction region, by means of gravity and/or positive pressure which e.g. is generated in the pipette tip by means of the second opening.

The transport container preferably consists partly or wholly of plastic. It is preferably a consumable article, which is typically only used for one treatment or a small number of treatment steps of the sample. However, the transport container can also consist partly or wholly of a different material.

The transport of a sample can be a transport of the sample from an initial position to a target position. The initial position may be present if the sample is disposed in a first sample container and the target position of this sample can be the position thereof in a second sample container, into which the sample is transferred. This type of transport is also referred to presently as sample transfer or transfer. In practice, a sample transfer is usually carried out in order to transfer a sample from a storage container, in which, for example, the sample was stored and/or which may, for example, contain a relatively large amount of the sample, into a second sample container, in which the sample is subjected to further treatment. This transport is, in particular, under program control, using at least one program parameter.

The transport container preferably is or can be connected to a transport apparatus of the laboratory machine.

A sample container can be an individual container, in which only a single sample is contained, or it can be a multiple container, in which a plurality of individual containers connected to one another are disposed.

The single container can be an open container or a sealable container. In the case of a sealable container, provision can be made for a covering element, in particular a sealing cap. The covering element can be securely connected to the container, e.g. as a hinged cover or hinged closure cap, or can be used as separate component.

In a multiple container, the plurality of single containers are preferably disposed in a fixed position with respect to one another, in particular disposed in accordance with the crossing points of a grid pattern. This simplifies the automated approach to the positions and, in particular, the individual addressing of samples. A multiple container can be embodied as plate element, in which the individual containers are connected in such a way that they form a plate-shaped arrangement. The individual containers can be embodied as depressions in a plate or can be interconnected by web elements. The plate element can have a frame element, in which the single containers are held. These connections between components can be integral connections, i.e. cohesive connections and/or connections generated by a common injection moulding process, or they can be generated in a force-fit and/or form-fit manner. In particular, the plate element can be a microtiter plate.

Multiple containers can comprise a plurality (2 to 10) of single containers. They can furthermore comprise a multiplicity (more than 10) thereof, typically 12, 16, 24, 32, 48, 64, 96, 384, 1536 single containers. In particular, the multiple container can be a microtiter plate. A microtiter plate can be embodied in accordance with one or more industrial standards, in particular the industrial standards ANSI/SBS 1-2004, ANSI/SBS 2-2004, ANSI/SBS 3-2004, ANSI/SBS 4-2004.

The maximum sample volume that can be held by a transport container or sample container typically lies between 0.01 ml and 100 ml, in particular 10-100 µl, 100-500 µl, 0.5-5 ml, 5-25 ml, 25-50 ml, 50-100 ml, depending on the type of selected transport container or sample vessel.

A sample container can comprise an information region, which can contain information about the sample container or the content thereof. The information region can contain encoded information, e.g. a barcode or QR code or an RFID chip, or information encoded differently. The information can have information for identifying the sample and/or a sample container. The laboratory machine can have an information reader for reading this information and preferably providing said information to the control apparatus.

The sample container preferably consists partly or wholly of plastic. It is preferably a consumable article, which is typically only used for one treatment or a small number of treatment steps of the sample. However, the sample container can also consist partly or wholly of a different material.

The sample container preferably can be transported by a transport apparatus of the laboratory machine.

The laboratory instrument, in particular the laboratory machine, is preferably embodied to treat a multiplicity of samples in succession and/or in parallel. In particular, a laboratory instrument, in particular the laboratory machine, is preferably embodied to treat, in particular to transport, to empty and/or to fill, a multiplicity of sample vessels, in particular single containers and/or multiple containers, in a program-controlled manner.

Preferably, a laboratory instrument, in particular the laboratory machine, comprises exactly one workspace. Such a laboratory instrument is compact and can be suitable, in particular, for use on a laboratory table, wherein, in that case, it is also referred to as, in particular, a table-top instrument. By way of example, the table can be the workbench of a chemical, biochemical or biomedical laboratory. The laboratory instrument can also be embodied for set up in such laboratory. A laboratory instrument with a workspace can furthermore be embodied as an independently operating instrument in such a laboratory or it can be included in an instrument assemblage.

The laboratory instrument, in particular the laboratory machine, can also be embodied as a laboratory line, in which a plurality of workspaces are disposed next one another in such a way that, by means of transport device, a single, a plurality or a multiplicity of samples can be transported successively and/or in parallel between the workspaces. A workspace of a laboratory line is preferably embodied in such a way that a specific laboratory object, usually relating to the parallel and/or sequential treatment of a multiplicity of samples, is carried out. A high work throughput of the laboratory line is obtained as a result of this specialization of each workspace. In order to perform such a specific object, provision can be made for only one type of treatment of at least one sample or for only a few types of treatment, e.g. two to ten treatment types, to be performed in each workspace. A treatment apparatus for performing a treatment, which is characteristic for a specific laboratory instrument, as described within the scope of the description of the invention, can be disposed at each workstation. The transport device can comprise a guide-rail system and/or a robotic apparatus for program-controlled movement of samples or sample containers.

A laboratory instrument, in particular a laboratory machine, can be connected or connectable to an LIMS. LIMS is an abbreviation for laboratory information and management system. As usual, an LIMS is a software system which relates to data processing in an automated or partly automated chemical, physical, biological or medical laboratory. Such data can originate from measurements of the samples and/or relate to the control of the data handling. An LIMS preferably serves for measurement value acquisition and measurement value evaluation. LIMS is used to increase the work throughput in a laboratory and/or to optimize the efficiency of the treatment of laboratory samples.

A workspace can preferably comprise a substantially planar, preferably horizontally disposed worktop. The workspace can comprise a plurality of predetermined workstations. A workstation can be assigned to a section of the workspace. This assignment can be fixed or can be determined by program control. A workstation can be fixedly configured or can be equipped differently.

The position of the workstations and/or the state of equipment of the workstation can be stored as information in the laboratory machine, in particular in the storage apparatus. This information can be used to enable the program-controlled treatment of samples which are disposed at predetermined positions of the workspace and which are to be treated at one or more of these workstations.

A workstation can serve for storing substances, e.g. for storing samples, cleaning means, waste.

A workstation can serve for storing tool elements.

A tool element can be e.g. a transport head for the fluid transfer, in particular a pipetting head, which can comprise a connection section for connecting one pipette tip (single channel pipetting head) or for connecting a plurality of pipette tips (multiple channel pipetting head). Liquid can be sucked into the at least one pipette tip if the latter is connected to the connection section by means of at least one pressure and gas-tight channel connected to the pipetting head. In the laboratory machine, this pipetting is performed, in particular, in a program-controlled manner; in particular, it is influenced by at least one program parameter. The transport head can also be a dispensing head which has at least one movement apparatus for moving a plunger of the dispenser tip. In the laboratory machine, the movement apparatus is moved, in particular, in a program-controlled manner; in particular, it is influenced by at least one program parameter. The transport head can serve for metering liquid, in particular for metering in different regions; a transport head can be embodied for metering a liquid sample with a volume that can be selected from a volume range specific to this transport head: e.g. 1-50 µL or 20-300 µL or 50-1000 µL, ("l" and "L" are each an abbreviation for litre). A transport head can be embodied as a single-channel head, in which only one sample is transported, or it can be embodied as a multi-channel head, in particular an eight-channel head or a 12-channel head, in which a plurality of samples are handled or transported in parallel. Preferably, provision is made for specific transport containers, which can be used depending on the respective type of transport head, in particular in accordance with the corresponding volume range.

A tool element can be e.g. a transport head for transporting objects, for example a carrier and/or gripper tool for carrying and/or gripping an object. A carrying tool can comprise a fastening section for detachably fastening the object to the carrying tool, e.g. by a force-fit and/or cohesive and/or magnetic connection between the object and the carrying tool. In this manner, it is possible within the work top or between a plurality of workspaces and/or work tops.

A tool element can furthermore be a treatment unit, e.g. for performing a thermal, acoustic, optical and/or mechanical treatment of at least one sample.

The laboratory instrument, in particular the laboratory machine, can comprise an information reader in order to read information regarding a sample and/or a sample container and/or a treatment instruction for this sample and/or this sample container and, preferably, make this available to the control apparatus of the laboratory machine.

The laboratory instrument, in particular the laboratory machine, preferably comprises at least one timer apparatus and/or preferably at least one timing apparatus in order to enable the time-dependent treatment of the samples. The time-dependent treatment is preferably controlled by a program, and, in particular, controlled by at least one program parameter.

In a preferred configuration of the laboratory machine according to the invention, the former is configured, as a function of the treatment type selected by the user and the program parameters entered by the user, to select automatically one or more the following components for use in the program-controlled treatment:

at least one suitable sample container, in particular suitable for holding a plurality of samples which are to be handled together, e.g. which are intended to be mixed or between which a chemical reaction or biochemical, biological or biomedical interaction is intended to occur;

at least one suitable transport container, in particular a pipette tip and/or a dispenser tip;

at least one suitable transport head, to which the preferably automatically selected transport container can be connected, at least one suitable tool element, which serves for performing the desired treatment.

Preferably, the laboratory machine according to the invention is configured, as a function of the treatment type selected by the user and the program parameters entered by the user, to select automatically one or more the following control parameters for use in the program-controlled treatment:

at least one period of time, during which a specific work step of the treatment is performed;

at least one sample volume and/or metering volume;

at least one work position of the at least one work top;

movement parameters for setting the motion sequence of the robotic apparatus of the laboratory machine required for the desired treatment of the sample.

As a result of the automatic selection of the aforementioned components and/or the control parameters as a function of at least one program parameter, in particular as a function of the at least one program parameter selected by the user, an advantage resulting for the user is that he does not need to individually determine the selection of the components and control parameters himself. Rather, the control parameters required for the treatment are selected by means of the program parameters entered by the user. The user needs no knowledge about the programming of the machine. As a result, the use of the laboratory machine is particularly convenient.

By way of example, what it is possible to achieve by the automatic selection of the aforementioned components and/or the control parameters as a function of at least one program parameter is that the correct pipetting head is selected automatically on the basis of the user specifications (e.g. dilute 20 samples) or, in more general terms, that the correct tool, e.g. transport head and/or tool head, is used. That is to say, the user then does not need to decide what the ideal tool is, but only needs to decide what the desired treatment is, e.g. nucleic acid purification in a desired manner. The user, e.g. a biologist, a biological assistant or a medical assistant, then merely needs to make those decisions which he can make easily and quickly due to his training, but does not need to be fluent in an abstract programming language or make relatively complicated calculations.

The treatment apparatus of the laboratory machine comprises: preferably at least one workspace, preferably at least one transport apparatus and preferably at least one treatment unit.

Preferably, the laboratory instrument, in particular the laboratory machine, has the property of permanently storing the program parameters entered by the user and to load these again automatically or following a user trigger. The user can then modify individual ones of the parameters in order to completely define a sample treatment type. As a result, the operating convenience is increased and the susceptibility to faults is decreased. This is advantageous against the backdrop that laboratory instruments are used particularly efficiently for repeating processes.

The laboratory instrument preferably comprises a user interface apparatus for the manual entry of data by a user and for displaying information, in particular information contained in this data, wherein the user interface apparatus comprises an indication apparatus, in particular a display, in particular a touchscreen display.

A laboratory instrument according to the invention is capable to work independently, i.e. as a stand-alone instrument, which means it may require some user input but does not require a data connection with a further device, e.g. a central control computer, in order to work in a conventional operating mode. The conventional operating mode of the laboratory instrument provides the treatment of the at least one laboratory sample using its treatment apparatus. Additionally, the laboratory instrument according to the invention is configured to handle the partial problem when it is operated as a part of the system according to the invention, in particular by receiving first treatment data and/or sending second treatment data. In particular, the control apparatus of a laboratory instrument is preferably capable to conduct the handling of the—overall-treatment process, during the processing, i.e. handling, of the partial problem. The further laboratory instrument, preferably, is capable to take over the control of the—overall-treatment process and continue the same during the subsequent processing, i.e. handling, of the further partial problem.

The laboratory instrument according to the invention can comprise a plurality of treatment apparatuses. The access control device according to the invention can be assigned to a plurality of laboratory instruments according to the invention, in particular connectable or connected thereto by means of a second interface apparatus and, in particular, second data connections. As a result, one access control device can enable the access of the users to more than one laboratory instrument or to a laboratory instrument with more than one treatment apparatus.

Further possible and preferred configurations of the method according to the invention can be derived from the description of the system according to the invention and of the laboratory instrument according to the invention and from the preferred configurations thereof.

Further preferred configurations of the system according to the invention and of the laboratory instrument according to the invention and of the method according to the invention emerge from the following description of the exemplary embodiments in conjunction with the figures and the description thereof. If nothing else is described or if nothing else emerges from the context, the same components of the exemplary embodiments are substantially characterized by the same reference signs. In detail:

Figure 1:
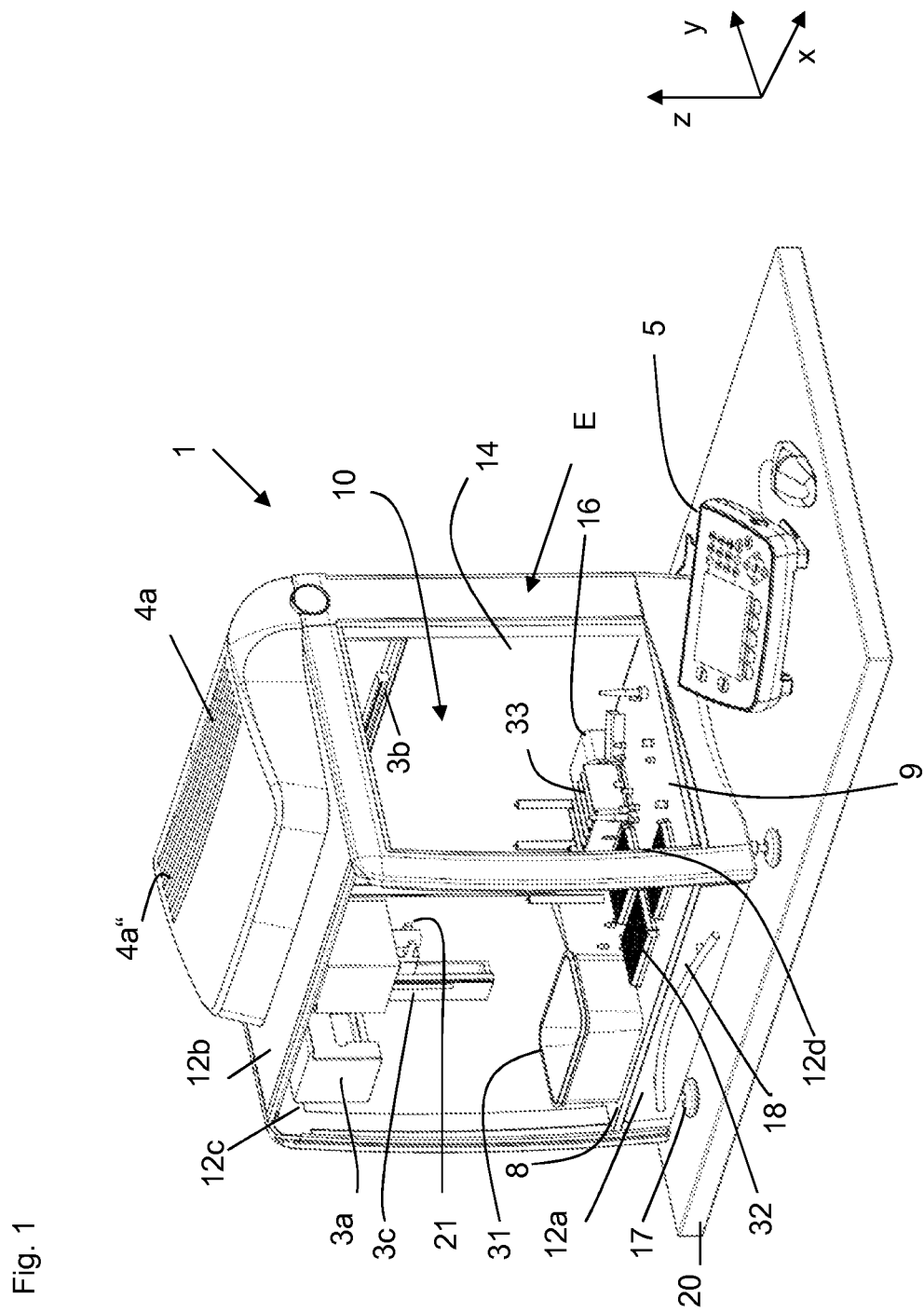
FIG. 1 shows an exemplary embodiment of the laboratory instrument according to the invention, which can be used in a system according to the invention.

FIG. 1 shows the laboratory instrument 1, which is embodied here as a laboratory machine 1 for treating fluid samples, to be precise as a pipetting machine. The laboratory machine 1 serves for the program-controlled treatment of these samples.

FIG. 1 shows the laboratory machine 1 for automated processing of liquid samples, in particular for the program-controlled treatment of liquid samples. The laboratory machine 1 is a table-top instrument and disposed on the work table 20 with the four feet 17 thereof. It comprises an electronic control apparatus 2 (not shown here), which is suitable for processing program code for the program-controlled treatment of the liquid samples. The control apparatus comprises at least one interface apparatus (not shown here) for establishing at least one data connection to at least one further laboratory instrument. The control apparatus is configured to receive first treatment data, which can be used for handling the partial problem, via the at least one interface apparatus, to perform the control of the handling of the partial problem using these first treatment of data, to provide, in particular generate, second treatment data as a function of the handling of the partial problem, which can be used by the further laboratory instrument for handling of a further partial problem of the treatment process, and to output at least these further treatment data for use by the further laboratory instrument via the at least one interface apparatus.

Figure 2A:
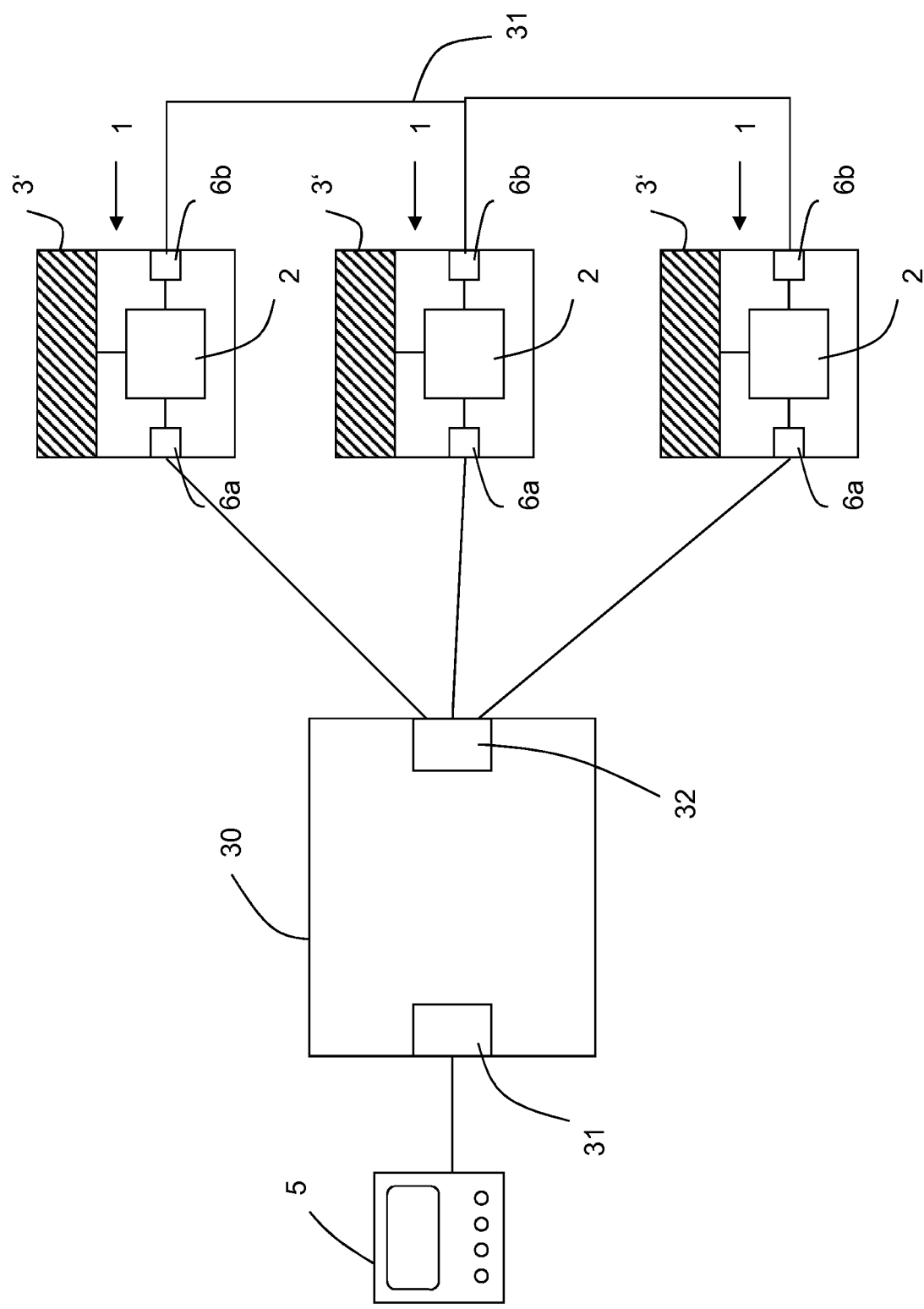
FIG. 2a shows a first exemplary embodiment of the system according to the invention, which comprises a server.
Figure 2B:
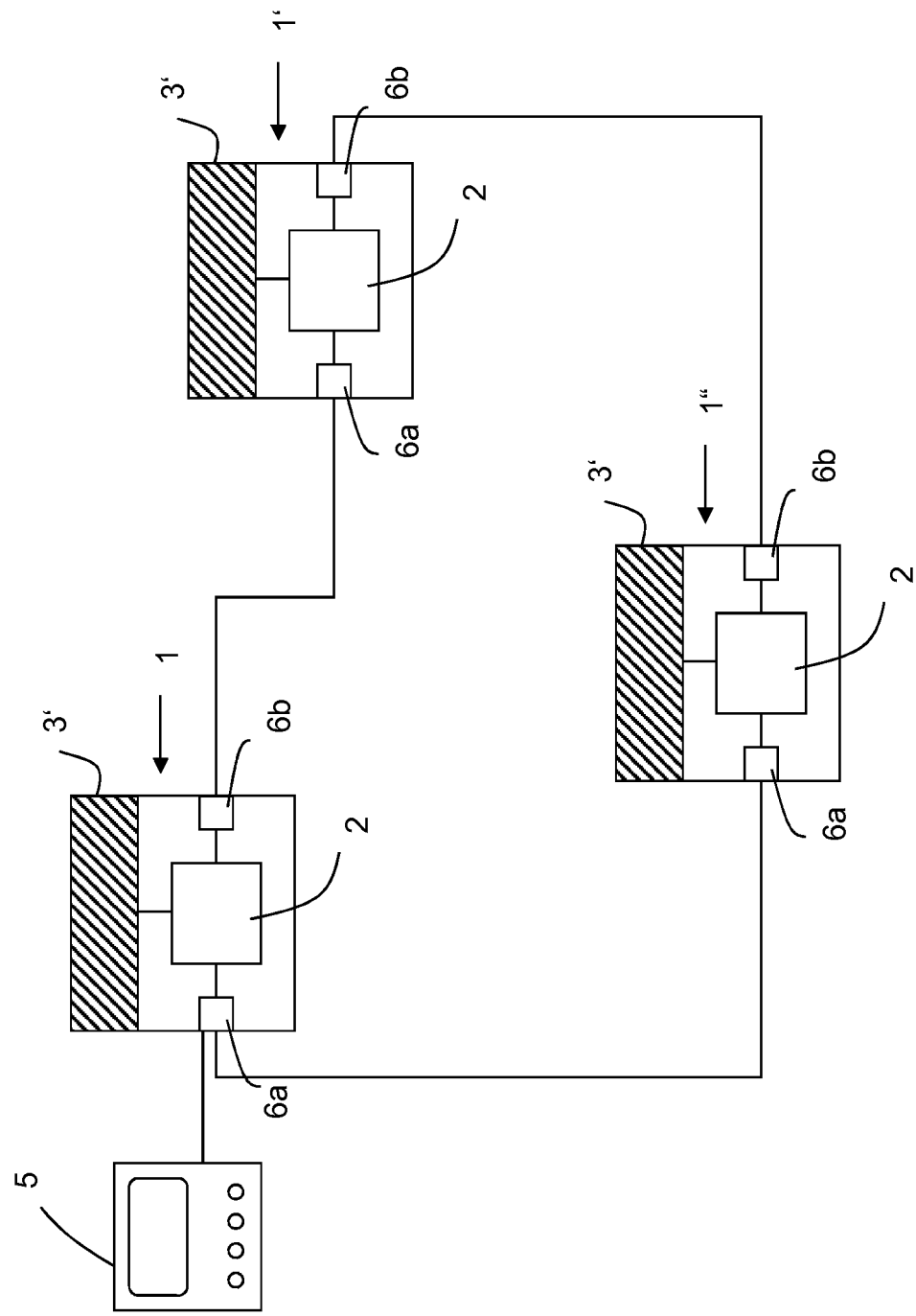
FIG. 2b shows a second exemplary embodiment of the system according to the invention, which does not comprise a server.

The laboratory machine 1 according to the invention can be used in a system according to the invention, e.g. the system shown in FIG. 2a or in FIG. 2b. The problem to be solved by the system may comprise to aliquot a defined liquid sample by means of a laboratory machine, to subsequently run a PCR on each partial sample using a thermocycler, and to subsequently store the resulting PCR samples in a freezer, in particular to electronically register the individual PCR samples in the control apparatus of the freezer. Processing such a problem becomes more efficient for the user using the system according to the invention, because the thermocycler automatically chooses a suitable PCR program containing appropriate temperature levels and/or cycle numbers, and/or automatically predefines and/or indicates suitable positions of the sample vessels in the sample block of the thermocycler, and because the freezer registers the individual PCR samples in the control apparatus of the freezer. Said advantages are achieved by the configurations of the laboratory instruments 1, 400 and 500 according to the invention and the configurations of the system of the invention according to FIG. 2a and FIG. 2b. Optionally and preferred, the one or more—or all—laboratory instruments determine the number and/or type of consumable used for handling a partial problem, and, respectively, include the respective data in the second treatment data. Such an embodiment is advantageous to improve logistics and book keeping in a laboratory, e.g. for possibly allowing for an automated ordering system for refilling consumables.

The laboratory machine 1 can, for example, extract from the first treatment data the information that a specific composition type of a liquid sample is provided, having predefined sample volumes of e.g. 6 ml, which are e.g. delivered in a defined 10 ml standard sample container at a receiving position defined by the user, wherein the partial problem found in the first treatment data is to distribute the overall sample volume to a number of e.g. ten separate standard-2 ml sample tubes. The second treatment data, which may be put out by the laboratory machine after finishing the handling of the first partial problem, may contain information on the specific composition type of the liquid samples, and on the finally produced number of standard-2 ml sample tubes and the respective amount of sample liquid in each standard-2 ml sample tube, and may contain information on the amount of consumables, which was used for handling the first partial problem, and may contain information on the overall status of processing the handling of the problem. The second treatment data are transferred from the laboratory machine 1 to the further laboratory instrument, which may be the thermocycler 400, via the interface apparatus of the laboratory machine 1 and the interface apparatus of the thermocycler 400.

Moreover, the laboratory machine 1 is configured as follows:

The control apparatus 2 is attached in the control space, which is denoted by the arrow E and separated from the workspace 10 by a vertical wall 14. The control space also harbours the voltage supply components which supply the suitable supply voltage for the electrical components of the laboratory machine. The control apparatus 103 of the access control device 100 from FIG. 1 is integrated into the control apparatus 2.

The laboratory machine 1 comprises a treatment space 10 for receiving the liquid samples to be treated, a sample handling apparatus 3, controllable in a program-controlled manner, for performing at least one program-controlled treatment step on the at least one sample, which is disposed in the handling space. The components 3a, 3b, 3c and 3d of the movement apparatus are assigned to the sample handling apparatus 3.

The laboratory machine 1 comprises a housing 12 comprising a front side 12a, a rear side 12f (not shown here) disposed opposite to the front side, a top side 12b, a bottom side 12d (not shown here) disposed opposite to the top side and two lateral sides 12c and 12d lying opposite one another. The sides 12a, 12b and 12c are substantially made of a material transparent to visible light.

The front side 12a, which is substantially embodied like door 12a, namely a sliding door 12a, can be moved by hand and/or moved in a program-controlled manner and can close downward, substantially along the z-axis of the Cartesian coordinate system. FIG. 2a shows the closed position of the door 12a.

The treatment space 10 is delimited by the front side 12a and the two side faces 12c and 12d, as well as the wall 14 and the worktop 8, which forms the upper side of the base plate 9. The worktop 8 provides six handling stations. The handling stations are substantially planar areas in the handling region 8. Pins serve to align the lab-ware, that is to say e.g. the thermorack 33, microtiter plates 32 and waste container 31, at the respective handling station. The exact positioning enables precise, robot-controlled addressing of the sample containers, in particular of the depressions in the microtitre plates 32. A magnetic separation device 16 is disposed in the vicinity of the wall 14, where a thermorack 33, i.e. a temperature-controlled sample vessel holder, is disposed. The magnetic fork (not shown here) of the magnetic separation device 16 enters corresponding receiving channels of the thermorack from the side in order to develop the magnetic effect thereof laterally on the laboratory vessels (sample tubules).

The laboratory machine 1 comprises two decontamination apparatuses, an electronically controllable air purification device 4a, 4a" for purifying the air in the treatment space, which is controlled electronically and digitally by the control apparatus and which comprises a ventilating device. The ventilation device comprises three ventilators (not depicted here), which transport an air flow from outside of the device into the treatment space.

The control apparatus 2 comprises a control program. The laboratory machine 1 comprises a sample handling apparatus 3, which comprises a movement apparatus with three guide-rail elements 3a, 3b, 3c, which correspond to movements along the y, x and z-axis of the Cartesian coordinate system. Electronically regulable linear motors are provided for driving the movement along the desired direction. In this manner, the assembly head 21 can be moved into each desired position accessible in the handling space 10. The movement apparatus is part of a robotic system of the sample handling apparatus 3. The assembly head 21 can be transported thereby in a program-controlled manner. A tool instrument, e.g. a pipetting head or a gripper, is connectable to the assembly head. The components disposed in the treatment space, in particular the sample processing apparatus 3, are components of the treatment apparatus of the laboratory machine.

The laboratory machine comprises a user interface apparatus 5, by means of which the user can log onto the laboratory machine locally.

Figure 4:
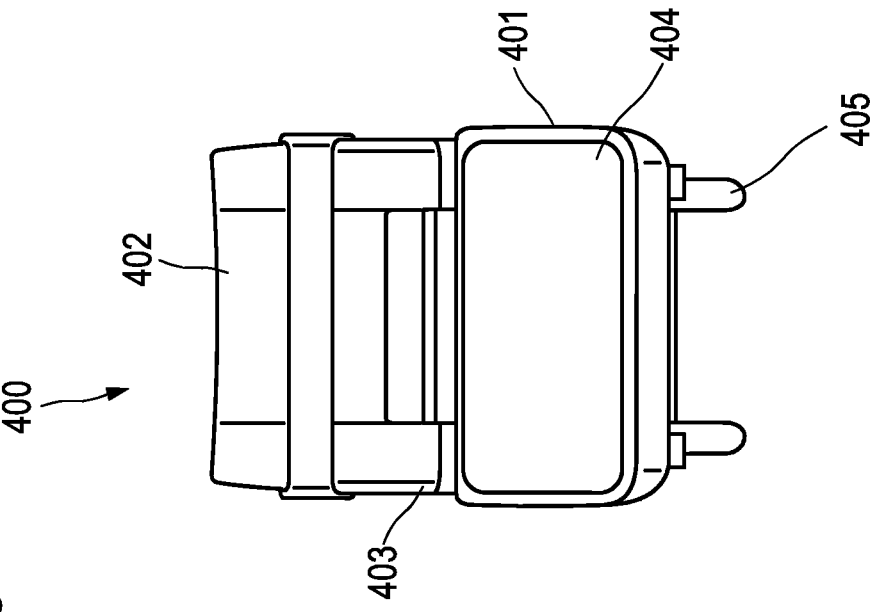
FIG. 4 shows a further exemplary embodiment of the laboratory instrument according to the invention, a thermocycler, which can be used in a system according to the invention.

FIG. 4 shows, as a further exemplary embodiment, the laboratory instrument 400, in this case a thermocycler. The laboratory instrument 400 is a tabletop instrument and disposed with feet 405 on a worktable (not depicted here). It comprises an electronic control apparatus 406 (not shown here), which is suitable for processing program code for the program-controlled treatment of the generally liquid samples. The treatment is usually a time-controlled temperature control. The control apparatus comprises at least one interface apparatus (not shown here) for establishing at least one data connection to at least one further laboratory instrument. The control apparatus is configured to receive first treatment data, which can be used for handling the partial problem, via the at least one interface apparatus, to perform the control of the handling of the partial problem using these first treatment of data, to provide, in particular generate, second treatment data as a function of the handling of the partial problem, which can be used by the further laboratory instrument for handling of a further partial problem of the treatment process, and to output at least these further treatment data for use by the further laboratory instrument via the at least one interface apparatus.

The control apparatus 406 is housed in the housing 401. The housing also harbours the voltage supply components which supply the suitable supply voltage for the electrical components of the laboratory instrument. The control apparatus 103 of the access control device 100 from FIG. 1 is integrated into the control apparatus 406.

The laboratory instrument 400 comprises a treatment space 403 for holding the liquid samples to be treated. The treatment space comprises at least one treatment apparatus 407 (not depicted here) for carrying out at least one program-controlled treatment step on the at least one sample which is disposed in the treatment space.

The control apparatus 406 comprises a control program.

The laboratory instrument comprises a user interface apparatus 404, by means of which a user can log onto the laboratory instrument locally.

The partial problem, solved by the thermocycler 400, may include choosing a suitable PCR program, for the purpose of automatically conducting a PCR of the sample solution in each of the ten standard-2 ml sample tubes. The thermocycler uses the information in the second treatment data related to the composition type of the liquid samples and derives the suitable PCR program from said information. The thermocycler conducts the PCR and puts out via its interface apparatus the further treatment data, here referred to as third treatment data, which are received by a freezer 500 via its interface apparatus. The thermocycler encodes in the third treatment data the information on the number and type of the PCR-sample vessels and the respectively amount of PCR samples in the PCR sample vessels, and may contain information on the number and type of consumables consumed by the laboratory machine 1 during handling of the first partial problem and the consumables consumed by the thermocycler 400 during handling of the second partial problem.

Figure 5:
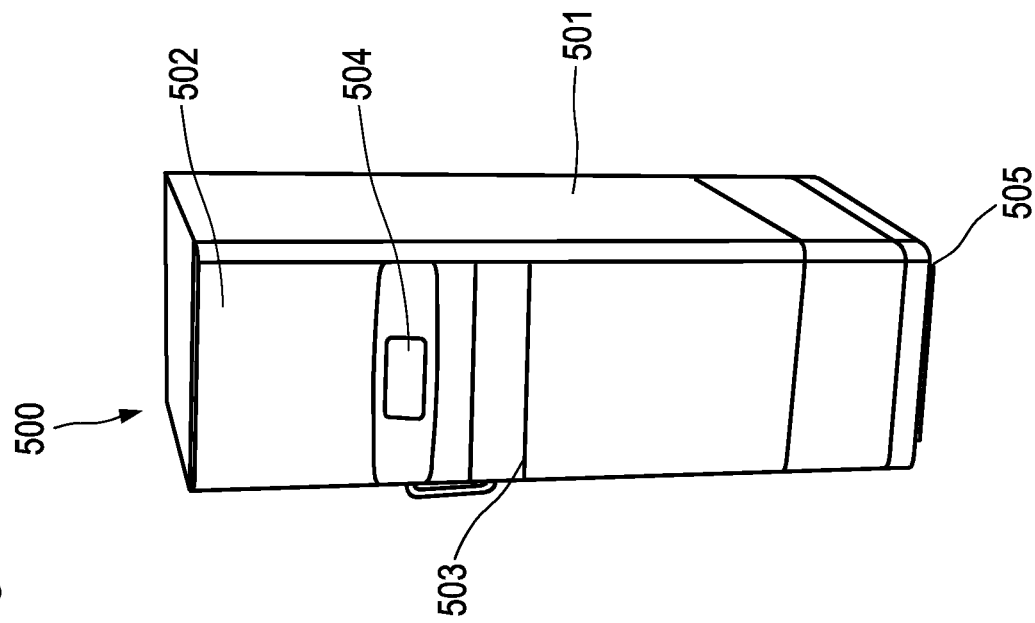
FIG. 5 shows, as a further exemplary embodiment of the laboratory instrument according to the invention, a laboratory freezer, which can be used in a system according to the invention.

FIG. 5 shows, as a further exemplary embodiment, the laboratory instrument 500, in this case a laboratory freezer. The laboratory instrument is a standing instrument which is positioned on the floor (not depicted here) with the feet 505. It comprises an electronic control apparatus 506 (not shown here), which is suitable for setting, regulating and monitoring the temperature of the laboratory instrument by program code. To process the treatment of the generally liquid samples. The treatment is usually permanent temperature control. The control apparatus comprises at least one interface apparatus (not shown here) for establishing at least one data connection to at least one further laboratory instrument. The control apparatus is configured to receive first treatment data, which can be used for handling the partial problem, via the at least one interface apparatus, to perform the control of the handling of the partial problem using these first treatment of data, to provide, in particular generate, second treatment data as a function of the handling of the partial problem, which can be used by the further laboratory instrument for handling of a further partial problem of the treatment process, and to output at least these further treatment data for use by the further laboratory instrument via the at least one interface apparatus. By way of example, first treatment data could represent information about the removal of one or more samples from the laboratory freezer and second treatment data could represent information about a preparation of the further laboratory instrument, e.g. preheating.

The control apparatus 506 is housed in the housing 501. The housing also harbours the voltage supply components which supply the suitable supply voltage for the electrical components of the laboratory instrument. The control apparatus 103 of the access control device 100 from FIG. 1 is integrated into the control apparatus 506.

The laboratory instrument 500 comprises a treatment space 503 for holding the liquid samples to be treated. The treatment space comprises at least one treatment apparatus 507 (not depicted here) for carrying out at least one program-controlled treatment step on the at least one sample which is disposed in the treatment space. The program-controlled treatment step in this case is the permanent temperature control at a defined temperature.

The control apparatus 506 comprises a control program.

The laboratory instrument 500 comprises a user interface apparatus 504, by means of which a user can log onto the laboratory instrument locally.

The partial problem handled by the freezer, referred to here as the third partial problem, may include deriving from the third treatment data one or more information about the individual PCR samples to be registered in the control apparatus of the freezer 500. The third partial problem may also include to store the information on the number and type of consumables, which were consumed during handling of the overall problem, and for example also to display said information, or to forward said information to an external server, which may be part of the system, but may also be externally arranged from the system.

Figure 3:
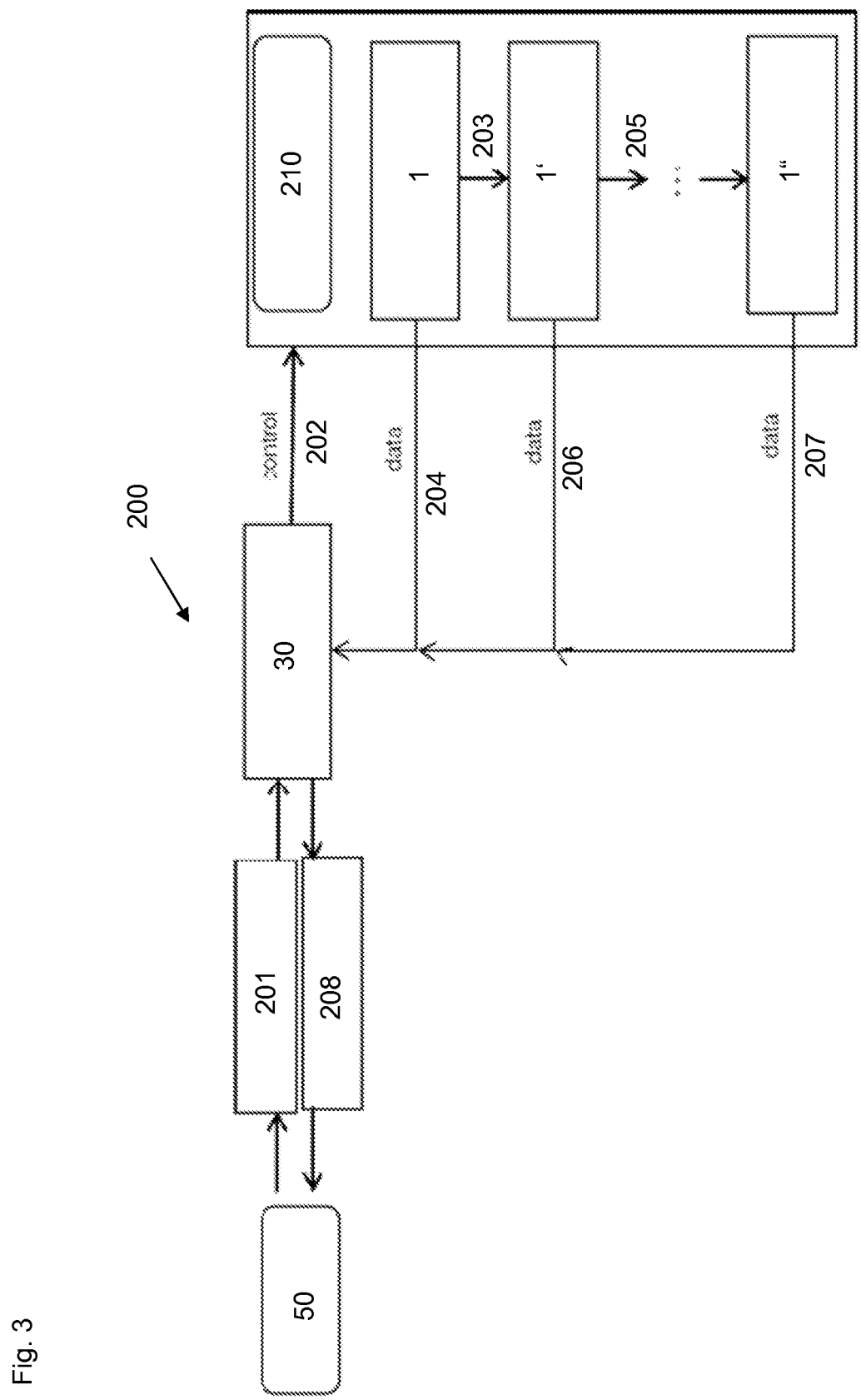
FIG. 3 shows an exemplary embodiment of a method according to the invention.

FIG. 2a shows a first exemplary embodiment of the system according to the invention, which comprises a server 30. In this example, the server 30 obtains the settings file from the user interface apparatus 5 via the interface apparatus 31 of the server, by means of which settings file the treatment process 210 (see FIG. 3) to be performed is defined. The settings file contains a number of parameters, by means of which the treatment process 210 to be performed is initially uniquely defined.

The server is connected to three different laboratory instruments 1, 1' and 1" via its interface apparatus 32. The laboratory instrument 1' could be a laboratory centrifuge and the laboratory instrument 1" could be a laboratory shaker with an incubator function. Each one of the laboratory instruments assumes a partial problem which is automatically or partly automatically handled by a treatment with the treatment apparatus 3'. The treatment process, which requires the use of the three laboratory instruments, is handled by the combined use of the three laboratory instruments. The laboratory instruments are respectively connected to the interface apparatus 32 of the server via an interface apparatus 6a and are, in the present case, additionally connected to one another via an interface apparatus 6b. Data can be interchanged by these connections, in particular first and/or second treatment data.

At the start of the method 200 according to the invention, the user 50 (see FIG. 3) transmits the settings file to the external data processing apparatus belonging to the system, i.e. to the server (step 201). In the process, the server authenticates the user via an access control device (not shown here) of the server. The server can then assign the first and second treatment data, which arise during the handling of the treatment process, to the user and perform a log file about the treatment process. As a result, the correctness of the performance of the treatment process can be documented.

The server 30 (FIG. 3) controls the progress of the treatment process by virtue of starting the latter and, in the process, transmitting first treatment data to the first laboratory instrument 1 (step 202). The laboratory instrument 1 requires these first treatment data in order to set and control the treatment of the first laboratory instrument 1. By way of example, the first treatment data can contain information about the sample number. In the process, the first laboratory instrument generates second treatment data which it transmits directly to the second laboratory instrument 1' via an interface 6b of the laboratory instrument (step 203). Simultaneously, these are transmitted to the server (step 204), where they are logged. By way of example, the second treatment data can contain the number of laboratory vessels with samples which are to be processed by the second laboratory instrument 1'. The second treatment data, which the laboratory instrument 1' generates during the second treatment and directly outputs to the third laboratory instrument 1" (step 205), serve as "first treatment data", which are required to perform the treatment in the laboratory instrument 1", for the laboratory instrument 1". Simultaneously, these are transmitted to the server (step 206), where they are logged. The third laboratory instrument 1" requires these treatment data for performing the third treatment and, in the process, generates "second treatment data". These are transmitted to the server (step 207), where they are logged. The server generates a log file from the collected treatment data. It is stored or transmitted to the user (step 208). In this method, essential process data are automatically interchanged, without the user needing to perform entries or calculations in this respect. As a result, the number of errors is reduced and the efficiency is increased. In particular, the consumption of commodities can be reduced to the required minimum by means of such a method.

FIG. 2b shows a second exemplary embodiment of the system according to the invention, which does not comprise a server. Here, via his user interface 5, the user enters the settings file directly into the first laboratory instrument, which likewise identifies the user via the access control device of the laboratory instrument. In this case, the data obtained in the settings file, in particular, form first treatment data. Treatment data can also be forwarded in this system. In particular, these can be merged during each forwarding in order to generate a log file. Similar advantages like in the exemplary embodiment of the system in accordance with FIG. 2a emerge.

The invention claimed is:

1. A laboratory instrument for the instrument-controlled treatment of a partial problem in a treatment process for handling at least one laboratory sample, which treatment process relates to the handling of a problem comprising partial problems when handling the at least one laboratory sample using the laboratory instrument and at least one further laboratory instrument, the laboratory instrument being configured to establish a direct data connection to the further laboratory instrument, the laboratory instrument and the further laboratory instrument being selected from the group of laboratory instruments including at least a centrifuge, a thermocycler, a biospectrometer, a cell counter, an incubator, a laboratory shaker, a laboratory mixer, a laboratory freezer, a bioreactor, a safety work bench, a biological safety cabinet, a sample plate reader, a laboratory machine for treating fluid samples, the laboratory instrument comprising:
a treatment apparatus for the instrument-controlled handling of the partial problem,
a control apparatus for controlling the laboratory instrument,
at least one interface apparatus for establishing at least one data connection to at least one further laboratory instrument;
wherein the control apparatus comprises a control program and is configured and programmed:
to receive first treatment data, which can be used for handling the partial problem, via the at least one interface apparatus and
to perform the control of the handling of the partial problem using these first treatment data,
to provide, in particular generate, second treatment data as a function of the handling of the partial problem, which second treatment data can be used by the further laboratory instrument for handling a further partial problem of the treatment process,
to forward the first treatment data and to merge the first treatment data with the second treatment data, and
to output at least further treatment data containing the first and second treatment data for use by the further laboratory instrument via the at least one interface apparatus by establishing a direct data connection between the interface apparatus of the first laboratory instrument and the interface apparatus of the further laboratory instrument within a restricted network of an intranet, wherein the further treatment data are transferred from the laboratory instrument to the further laboratory instrument without being processed by an interconnected data processing instrument being the control apparatus of a laboratory instrument, and
wherein the laboratory instrument comprises at least one clock or timing apparatus to provide a time-dependent handling of the partial problem and wherein the control apparatus is configured and programmed to perform the control of the handling of the partial problem using at least one program parameter depending on the clock or timing apparatus, wherein the first and the second treatment data respectively contain time data which contain information about the planned start and/or the end of a treatment using the treatment apparatus for the instrument-controlled handling of the partial problem.

2. A method for instrument-controlled handling of a partial problem in a treatment process for handling at least one laboratory sample, which treatment process relates to the handling of a problem comprising partial problems when handling the at least one laboratory sample using a laboratory instrument, wherein the laboratory instrument is configured according to claim 1, and the following steps of the method are carried out by means of the control apparatus of the laboratory instrument:

receiving first treatment data, which can be used for handling the partial problem, by means of the at least one interface apparatus, and
controlling the handling of the partial problem using these first treatment data,
providing, in particular generating, further treatment data as a function of the handling of the partial problem, wherein the further treatment data can be used by a further laboratory instrument according to claim 1 for handling a further partial problem of the treatment process, and
outputting at least these further treatment data via the at least one interface apparatus for use by the further laboratory instrument by establishing a data connection between the interface apparatus of the laboratory instrument and the interface apparatus of the further laboratory instrument within a restricted network of an intranet.

3. A method of using a laboratory instrument, the method comprising:
providing the laboratory instrument according to claim 1;
handling a problem by a treatment process for handling at least one laboratory sample, wherein the problem contains the handling of at least a first and a second partial problem, by means of said laboratory instrument.

4. The method of claim 3, the method further comprising:
arranging said laboratory instrument in a chemical, biological, biochemical, medical or forensic laboratory; and
performing the handling of the problem in said laboratory.

5. A system for instrument-controlled handling of a problem by a treatment process for handling at least one laboratory sample, wherein the problem contains the handling of at least a first and a second partial problem,
the system comprising:
at least one first laboratory instrument according to claim 1 comprising at least one treatment apparatus, a control apparatus and at least one interface apparatus for handling the first partial problem of the problem, and
at least one second laboratory instrument according to claim 1 comprising at least one treatment apparatus, a control apparatus and at least one interface apparatus for handling the second partial problem of the problem,
the first laboratory instrument being configured to establish a direct data connection to the second laboratory instrument,
wherein the first laboratory instrument is configured
to perform the control of the handling of the partial problem using first treatment data, wherein the system is configured:
to provide, in particular generate, second treatment data as a function of the handling of the first partial problem, which second treatment data can be used by the second laboratory instrument for handling the second partial problem of the treatment process, and
to output at least the second treatment data for use by the at least one second laboratory instrument by establishing a direct data connection between the interface apparatus of the first laboratory instrument and the interface apparatus of the second laboratory instrument, wherein said at least second treatment data are transferred from the first laboratory instrument to the second laboratory instrument without being processed by an interconnected data processing instrument being the control apparatus of a laboratory instrument,
wherein the second laboratory instrument is configured
to receive the second treatment data from the first laboratory instrument via said data connection within a restricted network of an intranet, which second treatment data can be used for handling the second partial problem, via the at least one interface apparatus thereof and
to perform the control of the program-controlled handling of the second partial problem using the second treatment data.

6. The system according to claim 5, comprising at least one external data processing apparatus, in particular a computer with a storage apparatus, in which first and/or second treatment data, which are used for performing the treatment process, can be stored.

7. The system according to claim 6, wherein the external data processing apparatus is configured to process first and/or second treatment data from at least one laboratory instrument of the system during the treatment process, in particular to receive treatment data from the first laboratory instrument and transmit treatment data to the second laboratory instrument.

8. The system according to claim 6 or 7, comprising at least one user interface apparatus, by means of which treatment data can be determined by a user, wherein the user interface apparatus is embodied to emit the treatment data to at least one laboratory instrument, in particular via the at least one external data processing apparatus.

9. The system according to claim 5, wherein at least one first laboratory instrument is configured to generate at least one first data record during the handling of a partial problem, which data record in particular contains information about the performance of the treatment in accordance with the first partial problem, in particular log data or consumable material-related data, and to output this data record as the first treatment data via the at least one interface apparatus, in particular to the at least one second laboratory instrument or an external data processing apparatus, and in that the system is configured to collect and store the at least one data record in a database.

10. The system according to claim 5, wherein the system is configured to store first and/or second treatment data during the treatment process and, from this, to generate and store a log file, in particular a certification file.

11. A method of using a system for instrument-controlled handling of a problem, the method comprising:
providing the system according to claim 5; and
handling a problem by a treatment process for handling at least one laboratory sample, wherein the problem contains the handling of at least a first and a second partial problem, by means of said system.

12. The method of claim 11, the method further comprising:
arranging said system in a chemical, biological, biochemical, medical or forensic laboratory; and
performing the handling of the problem in said laboratory.

13. The laboratory instrument according to claim 1, wherein the provided second treatment data contains information about the performance of the treatment in accordance with the partial problem, in particular log data or consumable material-related data.

14. The laboratory instrument according to claim 1, wherein the laboratory instrument is configured to store first and/or second treatment data during the treatment process and, from this, to generate and store a log file, in particular a certification file.

15. The laboratory instrument according to claim 1, wherein the first treatment data and/or the second treatment data contains time data about absolute times or about relative times.

16. The laboratory instrument according to claim 1, wherein the laboratory instrument is configured to permanently store the program parameters entered by the user and to load these again automatically or following a user trigger.

17. The method according to claim 2, using the system according to claim 5, which is configured to receive user data which are output to the system by the user via a user interface and the system is configured to define the treatment process from the user data by virtue of treatment data being generated as a function of the user data, wherein these treatment data influence, in particular control, the handling of the partial problems by the at least one first and second laboratory instrument.

18. The laboratory instrument of claim 1, wherein said control apparatus comprises a booking apparatus, which comprises a storage apparatus, which stores booking data, and wherein a booking data record of said booking data contains data at what time said laboratory instrument will carry out the treatment, and wherein said control apparatus is embodied to evaluate some or all booking data in accordance with an evaluation method stored in an storage apparatus to create the schedule according to at least one criterion.

19. The laboratory instrument of claim 1, wherein said control apparatus is integrated in a module which is securely connected to said laboratory instrument.

20. The system of claim 5, wherein one of its laboratory instruments comprises a conventional operating mode, in which it is capable to work independently and to provide the treatment of at least one laboratory sample using its treatment apparatus, and, additionally when said laboratory instrument is operated as part of the system according to claim 5, the laboratory instrument is configured to handle the partial problem and preferably the control apparatus is capable to conduct the handling of the overall treatment process during the handling of the partial problem.

21. The system of claim 5, wherein said control apparatus of one of its laboratory instruments is integrated in a module which is securely connected to said laboratory instrument.

22. The system of claim 10, the laboratory instruments of the system being embodied to receive, bundle and forward the treatment data required for performing the further treatment step to a further laboratory instrument of the system, the system being configured to provide the log file at the end of the treatment process, wherein the log data in the log file contain all first and/or second treatment data which are provided and/or generated by all laboratory instruments during the course of the treatment process.

23. The system of claim 22, wherein the log data contain all treatment data required for being able to unambiguously reproduce the treatment process with the system.

24. The system of claim 23, the system being configured to generate an electronic lab book based on the log data, by means of which the individual treatments of the treatment process are compiled and stored as a file depending on the identity of the user performing the treatments or the treatment process.

* * * * *